(12) United States Patent
Singh et al.

(10) Patent No.: US 6,552,216 B1
(45) Date of Patent: Apr. 22, 2003

(54) MOLECULAR MODEL FOR VLA-4 INHIBITORS

(75) Inventors: Juswinder Singh, Ashland, MA (US); Zhongli Zheng, Lexington, MA (US); Peter Sprague, Pennington, NJ (US); Herman Van Vlijmen, Somerville, MA (US); Alfredo Castro, Winchester, MA (US); Steven P. Adams, Andover, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/236,784

(22) Filed: Jan. 25, 1999

Related U.S. Application Data

(63) Continuation of application No. PCT/US97/13008, filed on Jul. 24, 1997.
(60) Provisional application No. 60/022,890, filed on Jul. 25, 1996, provisional application No. 60/032,786, filed on Dec. 6, 1996, and provisional application No. 60/057,002, filed on Jun. 30, 1997.

(51) Int. Cl.[7] .................. C07C 205/00; C07C 229/00; C07C 315/00; C07K 211/56; A61K 38/00

(52) U.S. Cl. .................. 560/22; 546/224; 560/34; 562/430; 562/437; 514/18

(58) Field of Search .................. 546/224; 560/21, 560/22, 34; 562/430, 437, 439

(56) References Cited

U.S. PATENT DOCUMENTS

| | | | |
|---|---|---|---|
| 4,725,583 A | 2/1988 | Luly et al. | |
| 4,826,815 A | 5/1989 | Luly et al. | |
| 4,908,360 A | 3/1990 | Martin et al. | |
| 5,260,277 A | 11/1993 | McKenzie | |
| 5,314,902 A | 5/1994 | Tjoeng et al. | |
| 5,403,836 A | 4/1995 | Blackburn et al. | |
| 5,434,188 A | 7/1995 | Boschelli et al. | |
| 5,770,573 A | 6/1998 | Arrhenius et al. | |
| 6,239,108 B1 | 5/2001 | Lin et al. | |
| 6,248,713 B1 | 5/2001 | Lin et al. | |
| 6,306,840 B1 | 10/2001 | Adams et al. | |

FOREIGN PATENT DOCUMENTS

| | | |
|---|---|---|
| DE | 43 09 867 | 9/1994 |
| EP | 0 0212 34 | 1/1981 |
| EP | 0 460 679 | 12/1991 |
| EP | 0 519 748 | 12/1992 |
| EP | 0 565 896 | 10/1993 |
| WO | WO 89/09786 | 10/1989 |
| WO | WO 91/09837 | 7/1991 |
| WO | WO 92/00995 | 7/1991 |
| WO | WO 92/08464 | 11/1991 |
| WO | WO 93/08823 | 11/1991 |
| WO | WO 93/09795 | 5/1993 |
| WO | WO 93/12809 | 7/1993 |
| WO | WO 94/02445 | 7/1993 |
| WO | WO 94/15958 | 1/1994 |
| WO | WO 94/23714 | 10/1994 |
| WO | WO 95/15973 | 12/1994 |
| WO | WO 96/22966 | 8/1996 |
| WO | WO 97/03094 | 1/1997 |

OTHER PUBLICATIONS

Taylor et al. "Peptide–Based Drug Design" Amer. Chem. Society, pp. 387–410, Washington DC 1995.* van Regenmortel, "Molecular design versus empirical discovery in peptide–based vaccines. Coming to terms with fuzzy recognition sites and ill–defined structure–function relationships in immunology," Vaccines, 2000, vol. 18, pp. 216–221.*

Abraham et al., $\alpha_4$–Integrins Mediate Antigen–induced Late Bronchial Responses and Prolonged Airway hyperresponsiveness in sheep, J. Clin. Invest. 1994, 93(2):776–787.

Bajusz et al., "Design and Synthesis of Peptide Inhibitors of Blood Coagulation", Folia Haematol. Leipzig, 1982, 109:16–21.

Baldwin et al., "An Efficient Substitute for the É–Aminoadipoyl Moiety of ê–(L–É–Aminoadipoyl)–L–Cysteinyl–D–Valine in the Enzymatic Synthesis of Penicillins", Tetrahedron, 1987, 43(18): 4217–4220.

Chen et al., Chemical Abstracts, 1991, 115: 159756r.

Chisholm et al., "Monoclonal antibodies to the integrin $\alpha$–4 subunit inhibit the murine contact hypersensitivity response", European Journal of Immunology, 1993, 23:682–688.

Elices et al., "Expression and Functional Significance of Alternatively Spliced CSI Fibronectin in Rheumatoid Arthritis Microvasculature", The Journal of Clinical Investigation, 1994, 93:405–416.

Ferguson et al., "Two integrin–binding peptides abrogate T cell–mediated immune responses in vivo", Proceedings of the National Academy of Sciences USA, 1991, 88:8072–8076.

Ferguson et al., "Antigen–Independent Processes in Antigen–Specific Immunity", The Journal of Immunology, 1993, 150:1172–1182.

Goodman et al., "Synthesis and Conformation of Sequential Polypeptides of L–alanine and beta–Aminobutyric Acid", Macromolecules, 1976, 9:1–6.

Gruszecki et al., "Diacylamine–perfekte Acylierungsmittel für die Peptidsynthese", Liebigs Ann. Chem., 1988, 331–336.

Hemler, "VLA Proteins in the Integrin Family: Structures. Functions. and Their Role on Leukocytes", Annual Review of Immunology, 1990, 8:365–400.

(List continued on next page.)

Primary Examiner—John S. Brusca
Assistant Examiner—Young Kim
(74) Attorney, Agent, or Firm—Fish & Richardson P.C.

(57) ABSTRACT

Pharmacophore models of VLA-4 inhibitors, methods of identifying novel inhibitors and novel inhibitors identified by these methods.

20 Claims, 25 Drawing Sheets

OTHER PUBLICATIONS

Jiang et al., "Approaches Toward the Total Synthesis of Astins A, B, And C", Tetrahedron Letters, 1994, 35:2121–2124.

Komoriya et al., "The Minimal Essential Sequence for a Major Cell Type–specific Adhesion site (CSI) within the Alternatively Spliced . . . ", Journal of Biological Chemistry, 1991, 266:15075–15079.

Lampi et al., "Comparison of Cell–Permeable Calpain Inhibitors and E64 in Reduction of Cataract in Cultured Rat Lenses", Toxicology and Applied Pharmacology, 1993, 117: 73–57.

Lobb et al., "The Pathophysiologic Role of $\alpha 4$ Integrins in Vivo", The Journal of Clinical Investigation, 1994, 94:1722–1728.

Molossi et al., "Blockade of Very Late Antigen–4 Integrin Binding to Fibronectin with Connecting Segment–1 Peptide Reduces Accelerated Coronary Arteriopathy . . . ", Journal of Clinical_Investigation, 1995, 95:2601–2610.

Morales–Ducret et al., "$\alpha_4\beta_1$ Integrin (VLA–4) Ligands in Arthritis Vascular Cell Adhesion Molecule–1 Expression in Synovium and on . . . ", The Journal of Immunology, 1992, 149:1424–1431.

Narumiya et al., "Pre–B cells adhere to fibronectin via interactions of integrin $\alpha 5/\alpha v$ with RGDS as well as of integrin $\alpha 4$ with two distinct V region sequences at its different . . . ", Intl. Immun., 1994, 6:139–147.

Nowlin et al., "A Novel Cyclic Pentapeptide Inhibits $\alpha 4\beta 1$ and $\alpha 5\beta 1$ Integrin–mediated Cell Adhesion", The Journal of Biological Chemistry, 1993, 268:20352–20359.

Sawyer, "Peptidomimetic Design and Chemical Approaches to Peptide Metabolism," *Peptide–Based Drug Design*, American Chemical Society, Washington, DC 1995, Chapter 17, pp. 387–410.

Subasinghe et al., "Synthesis of Acyclic and Dehydroaspartic Acid Analogues of Ac–Asp–Glu–OH and Their Inhibition of Rat Brain N–Acetylated alpha–Linked Acidic Dipeptidase (NAALA Dipeptidase)", Journal of Medicinal Chemistry, 1990, 33:2734–44.

Wayner et al., "Activation–dependent Recognition by Hematopoietic Cells of the LDV Sequence in the V Region of Fibronectin", The Journal of Cell Biology, 1992, 116:489–497.

Yednock et al., "Prevention of experimental autoimmune encephalomyelitis by antibodies against $\alpha 4\beta 1$ integrin", Nature, 1992, 356–63–66.

Goodman et al., The pharmacological basis of therapeutics. $6^{th}$ ed, New York, Macmillan Publishing Inc., 1980, 1738–1740.

Thierry et al. "Systhesis and Activity of NacSerAspLysPro Analogues on Cellular Interactions between T–Cell and Erythrocytes in Rosette Foudation" J. Med Chemistry 1990.

Greenstein et al. Chemical Procedures for Synthesis of Peptides The Chemistry of the Amino Acids vol. 2.

Kim et al. "Inhibition of I–Labeled Ristocetin Binding to Micrococcus luteus Cells by the Peptides Related to Bacterial Cell Wall Mucopeptide Precursors: Quantitive Structure–Activity Relationships" J. Med. Chemistry 1989.

* cited by examiner

ATOM-BASED VIEW

FEATURE-BASED DESCRIPTION

RELATIONSHIP BETWEEN FEATURE-BASED AND ATOM-BASED DESCRIPTION

QIDSP LOOP IN VACM

HYPOTHESIS BASED ON C=O OF Q38 AND CO2 OF D40

FIT OF THE X-RAY OF VCAM (38-42) TO THE VLA4 MODEL

M123  0.1135

M124  0.186

M125  1.655

M126  10.5

M127  2.265

M128  0.0643

M129  0.017

M130  0.005

M131  0.0095

M132  0.1905

M143 
M144

M145 
M146

M147 
M148

M149 
M150

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 1

Glu Ile Leu Asp Val Pro Ser Thr
 1               5

<210> SEQ ID NO 2
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 2

Glu Ile Leu Asp Val
 1               5

<210> SEQ ID NO 3
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 3

Leu Asp Val Pro Ser
 1               5

<210> SEQ ID NO 4
<211> LENGTH: 5
<212> TYPE: PRT
<213> ORGANISM: Artificial Sequence
<220> FEATURE:
<223> OTHER INFORMATION: Synthetically generated peptide
<221> NAME/KEY: VARIANT
```

```
<222> LOCATION: (4)...(4)
<223> OTHER INFORMATION: Xaa = TPro(4-thioproline)

<400> SEQUENCE: 4

Arg Cys Asp Xaa Cys
  1               5

<210> SEQ ID NO 5
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 5

Gln Ile Asp Ser Pro
  1               5
```

MOLECULAR MODEL FOR VLA-4 INHIBITORS

CROSS REFERENCE TO RELATED APPLICATIONS

This application is a continuing application of International Application No. PCT/US 97/13008, which was filed Jul. 24, 1997 and claimed the benefit of U.S. Provisional Application Nos. 60/022,890, 60/032,786, and 60/057,002, filed Jul. 25, 1996, Dec. 6, 1996, and Jun. 30, 1997, respectively.

The present invention relates to a novel pharmacophore model for identifying compounds that are useful for the inhibition, alteration or prevention of the binding of the integrin VLA-4 to its ligands. This invention also relates to methods of discovering molecules which may inhibit VLA-4 binding to its ligands as well as novel molecules which have features which map to the claimed models.

BACKGROUND OF THE INVENTION

In recent years, rational drug design has become a common approach to identifying new drugs in the pharmaceutical industry. This approach requires selecting a protein target molecule which plays a critical role in a physiologically relevant biological pathway. The chemist typically begins with the natural ligand as the lead and modifies it to produce a compound with the desired properties. The natural ligand or substrate of this protein is manipulated to produce an enzyme inhibitor, or an agonist or antagonist for a receptor, depending upon the identified therapeutic need, capitalizing upon knowledge of what is known about the mechanism of action of the protein-ligand complex.

Most cell receptors have a developed pharmacology of agents that act as agonists or antagonists. However, despite extensive pharmacological research and the development of many new methodologies and laboratory techniques, certain receptors, and/or their action still remain elusive and no desirable antagonists have yet been discovered to inhibit or modulate their activity.

Additionally, often certain agonists or antagonists of a particular cell receptor are known, however, there remains a need for methods of identifying new inhibitors, new molecular entities and methods to quickly and effectively determine whether a particular compound possesses a desired pharmacological activity.

Cell adhesion is one of the fundamental mechanisms underlying numerous biological phenomena, such as, for example, the adhesion of hematopoietic cells to endothelial cells, and the subsequent migration of those hematopoietic cells out of the blood vessels and to the site of injury. Thus, cell adhesion is known to play a role in numerous pathologies such as inflammation and immune reactions.

α4β1 integrin, also known as very late antigen-4 ("VLA-4"), is a leukocyte cell surface receptor that participates in a wide variety of both cell-cell and cell-matrix adhesive interactions. It serves as a receptor for the cytokine-inducible endothelial cell surface protein, vascular cell adhesion molecule-1 ("VCAM-1"), as well as to the extracellular matrix protein fibronectin. Results of several in vivo experiments suggest that the inhibition of VLA-4 dependent cell adhesion may prevent, inhibit or alter several inflammatory and autoimmune pathologies.

In order to identify the minimum active amino acid sequence necessary to bind VL-4, Komriya et al. snthesized a variety of overlapping peptides based on the amino acid sequence of the CS-region (the VLA-4 binding domain) of a particular species of fibronectin. ("The Minimal Essential Sequence for a Major Cell Type-Specifice Adhesion Site (CS1) Within the Alternatively Spilced Type III Conencting Segment Domain of Fibronectin Is Leucine-Aspartic Acid-Valine", J. Biol. Chem., 266 (23), pp. 15075–79 (1991). They identified an 8-amino acid peptide, SEQ ID NO:1 Glu-Ile-Leu-Asp-Val-Pro-Ser-Thr, as well as two smaller overlapping pentapeptides, SEQ ID NO:2 Glu-Ile-Leu-Asp-Val and SEQ ID NO:3 Leu-Asp-ValPro-Ser, that possessed inhibitory activity against FN-dependent cell adhersion. These results suggested that the tripeptide Leu-Asp-Val was the minimum sequence for cell-adhesion activity. It was later shown that Leu-Asp-Val binds only to lymphocytes that express an activated form of VLA-4, thus casting doubt on the utility of such a peptide in vito. (E. A Wayner et al., "Activation—Dependent Recognition by Hematopoietic Cells of the LDV Sequence in the V Region of Fibronectin", J. cell. Biol., 116(2), pp. 489–497 (1992)). However, certain larger peptides containing the LDV sequence were subsequently shown to be active in vivo (T. A. Ferguson et al., "Two Intergrin Binding Peptides Abrogate T-Cell-Mediated Immune Responses in Vivo", Proc. Natl. Acad. Sci. USA, 88, pp. 8072–76 (1991); and S. M. Wahl et al., "Synthetic Fibronectin Peptides Suppress Arthritis in Rats by Interrupting Leukocyte Adhesion and Recruitment", J. Clin. Invest., 94, pp. 655–62 (1994)).

A cyclic pentapeptide, SEQ ID NO:4 Arg-Cys-Asp-Tpro-Cys (wherein Tpro denotes 4-thioprline), which can inhibit both VLA-4 and VLA-5 adhesion to FN has also been described. (See, e.g., D. M Nowlin et al. "A Novel Cyclic Pentapeptide Inhibits α4β1 and α5β1 Integrin-mediated Cell-Adhesion", J. Biol. Chem., 268(27), pp. 20352–59 (1993); and PCT publication PCT/US91/04862. This pentapeptide was based on the tripeptide sequence Arg-Gly-asp from FN which had been know as a common motif in the recognition site for several extracellular-matrix proteins.

Examples of other VLA-4 inhibitors have been reported, for example, in copending United States patent application U.S. Ser. No. 08/376,372, specifically incorporated by reference herein. U.S. Ser. No. 376,372 describes linear peptidyl compounds containing β-amino acids which have cell adhesion inhibitory activity. International patent applications WO 94/15958 and WO 92/00995, specifically incorporated by reference, describe cyclic peptide and peptidomimetic compounds with cell adhesion modulating activity. International patent applications WO 93/08823 and WO 92/08464 (specifically incorporated by reference herein) describe guanidinyl-, urea- and thiourea-containing cell adhesion modulating compounds. U.S. Pat. No. 5,260,277 describes guanidinyl cell adhesion modulation compounds, and is also specifically incorporated herein.

As discussed above, it is desirable for several reasons to approach the discovery of new drugs in a rational as opposed to a random manner. Thus, rather than making random modifications to a compound, one can rationally optimize the compound.

Ideally, a three dimensional model of the binding mode of inhibitors to a receptor is sought such that a correlation between the structure of the compound and its effect on biological activity can be derived. Several general approaches exist for determining the three dimensional quantitative structure activity relationships of compounds and their receptors or ligands, including, but not limited to: CATALYST™ (Greene et al., 1994, "Chemical Function queries for Three dimensional database search", J. Chem. Inf. Comp. Sci., 34, 1297–1308), DISCO (Martin Y. C., et al., 1993, "A Fast new approach to pharmacophore mapping and its application to dopinergic and benzodiazepine agonists", J. Comp. Aided Mol. Design, 7, 83–102), COMFA (Cramer R. D., 1988, "Comparative molecular field analysis [COMFA] 1. Effect of Shape on Binding of Steroids to Carrier Proteins", J. Am. Chem. Soc., 110, 5959–5967), Apex3D (Golender, V. E. And Vorpagel, E. R., 1993, "Computer-assisted pharmacophore identification", Three dimensional-QSAR in Drug Design:Theory, Methods and Applications, ESCOM Science Publ., Netherlands). Once a three dimensional model is built it can be useful in identifying novel compounds. For example, Kiyama et al. were able to identify novel AII antagonists based upon a three dimensional model of known AII inhibitors. (1995, "Novel AII receptor antagonists. Design, synthesis, and in-vitro evaluation of dibenzo[a,d] cycloheptene and dibenzo[b,f] oxepin derivatives. Searching for bioisoteres of biphenyltetrazole using a Three dimensional search technique", J. Med. Chem., 38, 2728–2741).

In general, there are several fundamental forces which govern the molecular recognition between a drug and its receptor, including, for example, hydrogen-bonding forces, electrostatic and hydrophobic interactions. Until recently most descriptions of inhibitors have been based upon two dimensional atomic topology diagrams which describe chemical structures (e.g. indole ring, carbonyl oxygen). Although these diagrams may be useful, they are somewhat limited in the information that they provide regarding the details of the biological activity of compounds. The availability of additional information would aid chemists in identifying novel compounds with a particular biological activity relatively quickly, cheaply and with a relatively high level of success.

An alternative to the two dimensional atomic topology approach (Greene et al., 1994, "Chemical Function queries for Three dimensional database search", J. Chem. Inf. Comp. Sci., 34, 1297–1308) describes compounds on the basis of chemical features which take into account the type of binding interaction of the chemical substructure. (FIG. 1; e.g. H-bonding donor, hydrophobe). One advantage of this approach is that it allows for a more general description of compounds, and accounts for its possible interactions with a receptor. The recognition that alternative chemical structures can present the same chemical features is central to drug discovery.

Examples of the use of the feature-based description of compounds to describe potent antagonists which differ in chemical structure but are similar in the chemical features they present exist. These include, for example, angiotensin converting enzyme antagonists (Sprague, 1994, "Building a hypothesis for Angiotensin Converting Enzyme Inhibition", MSI Inc., 16 New England Executive Park, Burlington, Mass. 01803) and $A_2$ antagonists (Sprague, 1994, "Building a hypothesis for AII Antagonism", MSI Inc., 16 New England Executive Park, Burlington, Mass. 01803).

Despite these advances, there remains a need for a model of a VLA-4 inhibitor which can be used to identify new specific inhibitors of cell adhesion, particularly for methods of identifying novel, specific inhibitors of VLA-4 cell adhesion. The availability of additional information would aid those skilled in the art to identify novel compounds with a particular biological activity quickly, inexpensively, and with a relatively high level of success. Ideally, such methods would allow practitioners to predict the inhibitory activity of novel compounds which would provide useful agents for treatment, alteration, prevention or suppression of various pathologies mediated by cell adhesion and VLA-4 binding.

SUMMARY OF THE INVENTION

Accordingly, the present invention is directed to a model of a VLA-4 inhibitor, methods of identifying new inhibitors, and new compounds which inhibit VLA-4 activity which map to the model, which substantially obviate one or more of the problems due to the limitations and disadvantages of the related art.

To achieve the features and advantages of the invention, as embodied and broadly described herein, the present invention relates to a three dimensional pharmacophore model of a compound having VLA-4 inhibitory activity. The claimed model 1 comprises certain features defined by the following tolerance and three dimensional coordinates x, y and z. Specifically the model comprises NEG ("N")

| | Feature | x (Å) | y (Å) | z (Å) | tolerance (Å) |
|---|---|---|---|---|---|
| N | NEG | −8.564 | 1.564 | −0.236 | 1.702 | and at least three features selected from the group consisting of

| | Feature | x (Å) | y (Å) | z (Å) | tolerance (Å) |
|---|---|---|---|---|---|
| 1 | HBA-1 | −1.276 | −1.259 | −1.47 | 1.702 |
| | HBA-2 | −2.323 | 1.539 | −1.35 | 1.702 |
| 2 | HBD-1 | 6.693 | 1.988 | −0.168 | 1.702 |
| | HBD-2 | 7.217 | 0.939 | 2.630 | 2.302 |
| 3 | HYD2 | 2.777 | −1.061 | −1.1501 | 1.702 |
| 4 | HYD3 | −3.803 | −4.061 | 0.270 | 1.702 |
| 5 | HYD4 | 9.377 | 2.219 | 1.050 | 1.702 |
| 6 | HYD5 | 8.677 | 4.439 | −1.330 | 1.702 |
| 7 | HYD6 | −9.123 | −1.501 | 1.110 | 1.702 |

The coordinates of the claimed models define the relative relationship between the features, and therefore those skilled in the art will readily recognize that the specific coordinates are dependent upon the particular coordinate system used, and thus, although rotation or translation of these coordinates may change the specific values of the coordinates, the coordinates will, in fact, define the claimed models.

Those skilled in the art should recognize that the claimed models are not without standard error. Thus, the claimed models are intended to encompass any model comprising the identified features and having a root mean square of equivalent features of less than about 2 Å.

More specifically, the model 1 of the invention comprises the negative ionizable feature "NEG", and at least four features selected from the group consisting of features 1–7. In other embodiments, the model may encompass 5–7 of the features, in addition to NEG.

In other embodiments, the applicant's invention relates to compounds which "map" to the claimed model. As used herein, the terms "map" and "fit" are used interchangeably to denote the correspondence between some or all of the features in a hypothesis and the chemical substructure of a particular conformer of a compound that satisfy those features, as computed by "catalyst" ("Hypothesis in Catalyst," MSI Inc., New England Executive Park, Burlington, Mass. 01803; Greene, I., 1994, J. Chem. Inf. Sci., "Chemical Function Queries for 3D Database Search," 34, 1297–1308). In additional embodiments, compounds having an $IC_{50}$ value in a VLA-4 direct binding assay in the range of from about 100 μm to about 1 μm, and which comprise features which map to NEG, and an additional 3–7 features of the model, are encompassed.

In yet other embodiments, applicants have discovered novel methods for identifying chemical compounds having an $IC_{50}$ value in a VLA-4 direct binding assay in the range of from about 100 μM to about 1 μM. The methods of the invention generally encompass selecting an experimental compound structure to be evaluated for VLA-4 inhibitory activity. The three dimensional structure of said compound is then obtained, and the structure of the experimental compound is then superimposed upon the VLA-4 model of the invention and evaluated to determine if the experimental compound "fits" the model. If the experimental compound fits the model, it is then tested in a direct binding assay to determine whether or not said experimental compound has the desired inhibitory activity. The compounds of the invention preferably have an inhibitory activity in the range of about 100 μM to about 0.5 nM, preferably of less than about 50 μm, more preferably less than about 500 nM, and most preferably, less than about 50 nM.

In yet other embodiments, the claimed invention relates to model 2, a three dimensional pharmacophore model of a compound having VLA-4 inhibitory activity. Model 2 comprises Neg ("N") as defined below, and at least four of features 1 through 8.

| | Feature | x (Å) | y (Å) | z (Å) | tolerance (Å) |
|---|---|---|---|---|---|
| N | NEG | 5.19 | 2.48 | −0.84 | 1.5 |
| 1 | HBA1-1 | 2.625 | 0.078 | −0.451 | 1.5 |
| | HBA1-2 | 1.434 | 2.840 | −0.448 | 1.5 |
| 2 | HBA2-1 | 6.038 | −1.968 | −0.039 | 1.5 |
| | HBA2-2 | 8.314 | −2.560 | 1.832 | 1.5 |
| 3 | HBD-1 | −6.17 | −0.82 | 0.767 | 1.5 |
| | HBD-2 | −6.606 | −3.3 | 2.412 | 1.5 |
| 4 | HYD2 | −1.126 | −0.54 | 1.532 | 1.5 |
| 5 | HYD3 | 1.054 | −3.780 | −2.528 | 1.5 |
| 6 | HYD4 | −8.786 | −1.3 | 1.972 | 1.5 |
| 7 | HYD5 | −8.786 | −0.580 | −0.788 | 1.5 |
| 8 | HYD6 | 8.594 | 2.12 | −3.428 | 1.5 |

Preferably, the model comprises at least 5 to 8 of the features 1–8 of Model 2. Additionally, applicants invention relates to compounds which fit Model 2 and have features which map to between 4 and 8 of the features of Model 2. The compounds of the invention preferably have an inhibitory activity in the range of about 100 μM to about 50 nM, preferably of less than about 50 μm, more preferably less than about 500 nM, and most preferably, less than about 50 nM.

In other embodiments, the claimed invention relates to methods for identifying chemical compounds having VLA-4 inhibitory activity using Model 2 in a manner similar to that described above for Model 1, as well as to compounds obtained by the claimed methods.

In still other embodiments, the claimed invention relates to a third three dimensional pharmacophore model of a compound having VLA-4 inhibitory activity. Model 3 comprises the following features:

| Feature | x (Å) | y (Å) | z (Å) | tolerance (Å) |
|---|---|---|---|---|
| Carboxyl C | −3.131 | −2.023 | 2.824 | 1.2 |
| Carboxyl O1 | −3.513 | −0.027 | 4.108 | 0.9 |
| Carboxyl O2 | −1.487 | −0.895 | 4.167 | 0.9 |
| Carbonyl C | −2.241 | 2.730 | 0.315 | 0.9 |
| Carbonyl O | −3.067 | 3.241 | 1.064 | 0.9 |

As discussed above in relation to Models 1 and 2, the invention also encompasses methods for identifying desired compounds using Model 3, as well as novel compounds which map to Model 3. Preferably, the novel compounds encompassed by the claims have the preferred $IC_{50}$ values discussed above.

It is to be understood that both the foregoing general description and the following detailed description are exemplary and explanatory and are intended to provide further explanation of the invention as claimed. The accompanying drawings are included to provide a further understanding of the invention and are incorporated in and constitute a part of this specification, illustrate several embodiments of the invention, and together with the description serve to explain the principles of the invention.

DETAILED DESCRIPTION

Reference will now be made in detail to the present preferred embodiments of the invention, examples of which are illustrated in the accompanying drawings.

Figure 1:
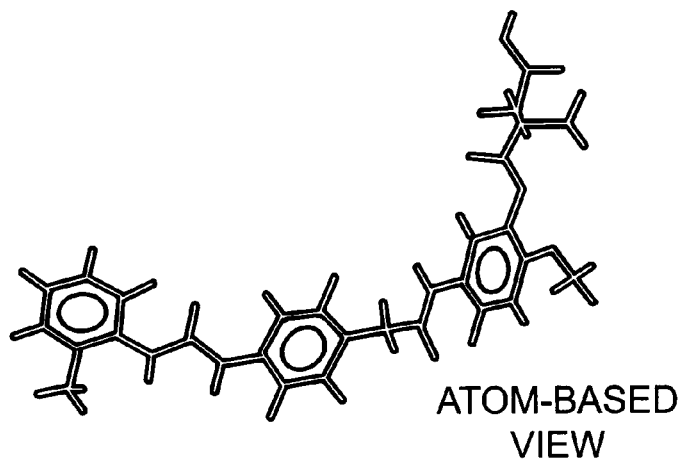
FIG. 1. Atom and Feature-based description of the compound M14. The atom-based description shows the three dimensional arrangement of atoms and bonds of M14.
Figure 1:
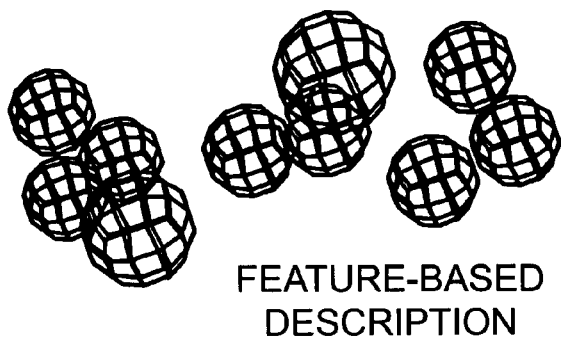
Figure 1:
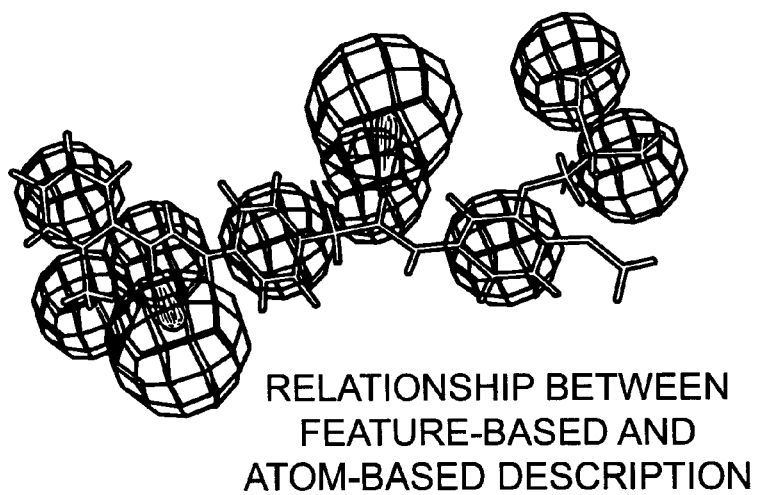

Applicants have invented 3-dimensional models which consist of the chemical features needed for a compound to inhibit the binding of ligands to the VLA-4 receptor. The models are generated from structure-activity data and are descriptions of chemical substructures or features that are important for biological activity within a class of molecules. Molecules that can present certain of the chemical features in a relative three dimensional orientation as described by the models are predicted to have VLA-4 inhibitory activity as measured by a VLA-4 direct binding assay (DBA) and may therefore have therapeutic potential. The models are feature-based, describing compounds on the basis of chemical features which take into account the type of binding interaction of the chemical substructure (Greene et al., 1994, "Chemical Function queries for Three dimensional database search", J. Chem. Inf. Comp. Sci., 34, 1297–1308). (FIG. 1; e.g. H-bonding donor, hydrophobe). One advantage of this approach is that it allows for a more general description of compounds, and accounts for possible interactions with a receptor. The recognition that alternative chemical structures can present the same chemical features is central to drug discovery. Examples exist of the use of the feature-based description of compounds to describe potent antagonists which differ in chemical structure but are similar in the chemical features they present. These include, for example, angiotensin converting enzyme antagonists and AII antagonists. (Sprague, 1994, "Building a hypothesis for AII Antagonism", MSI Inc., 16 New England Executive Park, Burlington, Mass. 01803).

The models of the invention provide those skilled in the art with a tool for discovering novel VLA-4 inhibitors, and thus, can be used to evaluate compounds prior to synthesis as to their ability to inhibit ligand binding to the VLA-4 receptor, or to design new compounds. The compounds being evaluated are referred to herein as "experimental compounds". More specifically, those skilled in the art will find that the claimed models can be used in conjunction with a computational computer program, such as, for example, Catalyst™, to search through chemical databases for chemical substructures of "experimental compounds" that might fit all or part of the model, and use the information so gathered to determine whether the experimental compound is likely to have VLA-4 inhibitory activity. Additionally, the claimed invention can provide the artisan with a tool to compare various experimental compounds not only with the claimed model, but with other experimental compounds. In other embodiments, those skilled in the art may use the claimed invention in combination with other software programs, such as, for example Denovo design software programs (e.g. Leapfrog "Ligand-Based Design Manual", Tripos Inc., 1699 S. Hanley Road, St. Louis, Mo. 63144–2913 ) to identify templates or chemical substructures which fit all or part of the model, and thereby determine the quality of the "fit". "Fit" is used herein to denote the correspondence between some or all of the features of an experimental compound to a reference model. In yet other embodiments, the claimed invention can be used by the artisan as a basis for intuitively designing novel VLA-4 inhibitors.

Figure 2:
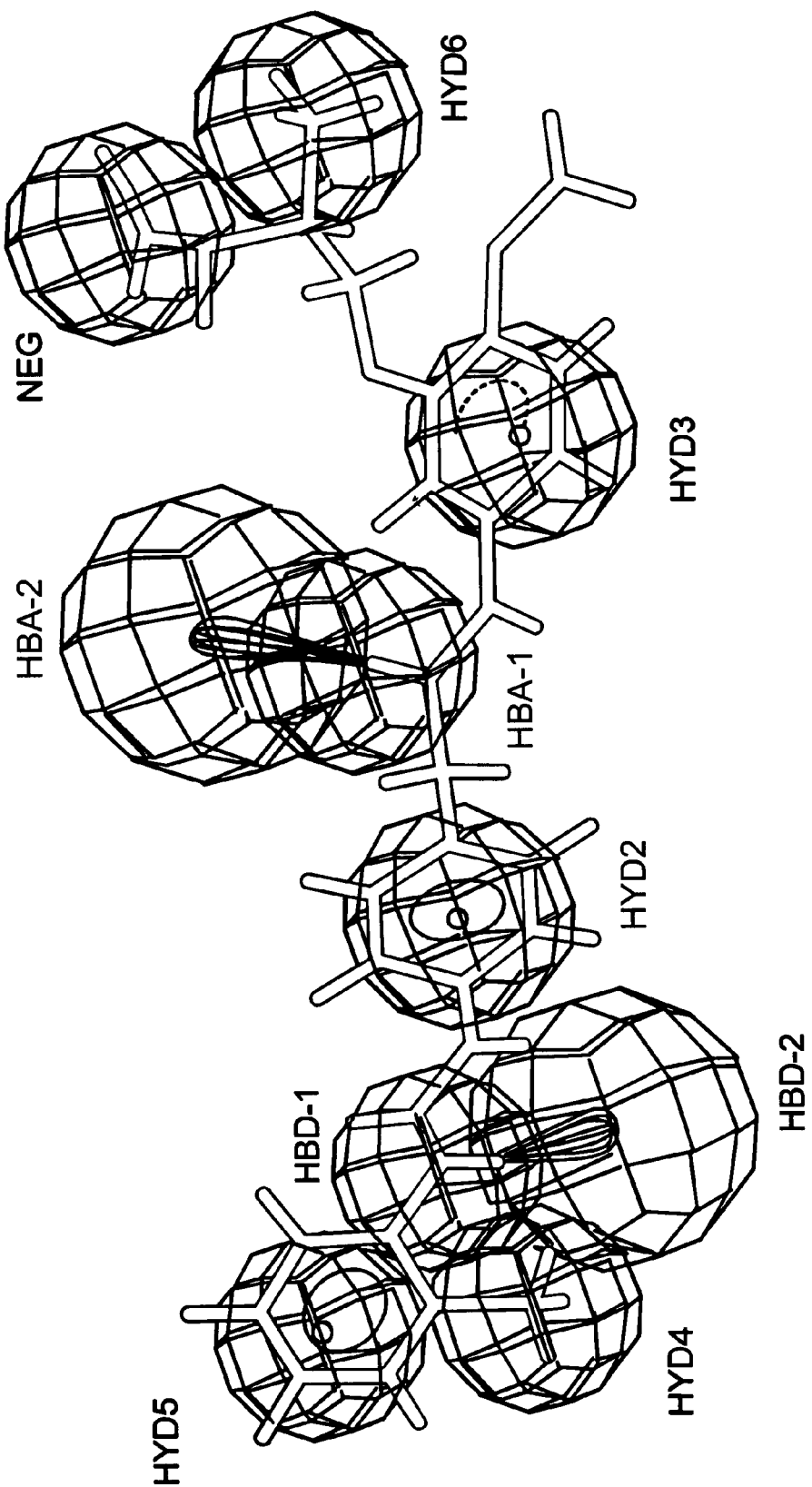
FIG. 2. The overlay, as computed by Catalyst, between M14 and the claimed VLA-4 Model 1. The features of the model have been labeled.

The claimed invention relates to a feature based three dimensional VLA-4 model which can be used to identify novel VLA-4 inhibitors. FIG. 2 shows the claimed VLA-4 model 1. As depicted, the model 1 consists of a set of features arranged in three dimensional space. Each feature is a definition of a chemical property of functional groups on molecules. Thus, as illustrated in FIG. 2, the relationship of chemical structures and features is given. Complete definitions of these features have been published, and can easily be understood by one skilled in the art. See, for example, Greene, J., Kahn, S., Savoj, H., Sprague, P., and Teig, S., 1994, "Chemical Function Queries for Three dimensional Database Search", J. Chem. Inf., and Comp. Sci., 34, 1297–1308, specifically incorporated herein by reference. The Cartesian coordinates of the claimed models can be defined mathematically by the x, y and z axes, and associated tolerance values. Unless otherwise stated, all Cartesian coordinates given herein are measured in angstroms.

A. Pharmacophore Models i) Model 1

The claimed model 1 comprises features defined by the following tolerance and three dimensional coordinates x, y and z. Specifically, Model 1 comprises NEG ("N") as defined below

| Feature | x (Å) | y (Å) | z (Å) | tolerance (Å) |
|---|---|---|---|---|
| N | NEG | −8.564 | 1.564 | −0.236 | 1.702 | and at least three features selected from the group consisting of

| | Feature | x (Å) | y (Å) | z (Å) | tolerance (Å) |
|---|---|---|---|---|---|
| 1 | HBA-1 | −1.276 | −1.259 | −1.47 | 1.702 |
|   | HBA-2 | −2.323 | 1.539 | −1.35 | 1.702 |
| 2 | HBD-1 | 6.693 | 1.988 | −0.168 | 1.702 |
|   | HBD-2 | 7.217 | 0.939 | 2.630 | 2.302 |
| 3 | HYD2 | 2.777 | −1.061 | −1.1501 | 1.702 |
| 4 | HYD3 | −3.803 | −4.061 | 0.270 | 1.702 |
| 5 | HYD4 | 9.377 | 2.219 | 1.050 | 1.702 |
| 6 | HYD5 | 8.677 | 4.439 | −1.330 | 1.702 |
| 7 | HYD6 | −9.123 | −1.501 | 1.110 | 1.702 |

The claimed model, in certain broad embodiments comprises the feature referred to as "Neg", i.e. a negative ionizable feature, and, in different embodiments, from three to seven of the seven features described above. It should be noted that, as used herein, the hydrogen-bond acceptor feature, HBA, Feature # 1, although encompassing both HBA-1 and HBA-2, is considered a single feature. Similarly, the HBD or hydrogen-bond donor feature, Feature # 2, is discussed as a single feature herein, although it encompasses both HBD-1 and HBD-2. "Hyd" as used herein refers to the Hydrophobic features.

The coordinates of Model 1 and the other Models claimed herein define the relative relationship between the features. Furthermore, the coordinates are dependent upon the particular coordinate system used, and those skilled in the art will recognize that, although rotation or translation of these coordinates may change the specific value of the coordinates, they will in fact define the claimed Models. The claimed Models are intended to encompass any model, after optimal superimposition of the models, comprising the identified features and having a root mean square of equivalent features of less than about 2 Å. More preferably, the claimed model encompasses any model comprising the identified features and having a root mean square of equivalent features of less than about 1.5 Å, and most preferably, less than about 1.0 Å.

The VLA-4 model can be used to evaluate the ability of a compound to inhibit the binding of VLA-4 to its receptor. The compound evaluated for inhibitory activity, the "experimental compound" can be a novel structure designed using the claimed model, or, alternatively can be a structure known in the art. Using the claimed model and methods, and the teachings herein, those skilled in the art can predict that an experimental compound which "fits" or "maps" to the model will have VLA-4 inhibitory activity.

In practice, the claimed model can be used in a variety of ways. For example, the claimed model can be used according to the claimed methods to identify novel VLA-4 inhibitors. First, one identifies an experimental compound to be evaluated for VLA-4 activity. This can be done for example, by searching a chemical database, or by modifying an existing compound. Alternatively, one can create a novel experimental compound. Those skilled in the art routinely utilize computer databases for searching, and computationally creating and/or modifying compounds.

After identifying an experimental compound to be evaluated for VLA-4 inhibitory activity, the three dimensional structure of the experimental compound is determined. One can use computer programs such as, for example, Catalyst™ software, however, one is not limited to this software. By way of example, the compound is drawn using the drawing tools in Catalyst™ and 3-dimensional conformations can then be generated using, for example, the Best conformer generation process with energy set to 10 Kcal/molss and the maximum number of conformations generated being set to 250. The model is then fit to the experimental compound using tools which can compare the two structures, such as, for example, Compare within the ViewHypothesis workbench.

The "fit" can be calculated automatically, for example, by determining if the compound can map to the chemical features in the model. This is dependent on whether the compound has the necessary or desired functional groups, and also whether they can adopt the necessary three dimensional arrangement to fit the model. The program can automatically report which features in the model are mapped by a compound. A "fit" as used herein means that the experimental compound must include the negative ionizable feature, and at least three others of the 7 features in the model are mapped.

If the experimental compound fits or maps the model, then one can experimentally determine whether that compound has the desired VLA-4 inhibitory activity by performing a direct binding assay (DBA). Those skilled in the art routinely perform such assays, and can readily determine the activity of the experimental compound.

In preferred embodiments, the claimed invention encompasses VLA-4 inhibitors having a commercially useful selectivity and specificity. These values may vary widely, however, are easily determined by those skilled in the art based upon the desired application of the inhibitor. In general, the inhibitors of the invention have an $IC_{50}$ value of less than about 100 μm in a VLA-4 direct binding assay. More preferably that value is less than about 50 μm, more preferably less than about 1 μm, In yet more preferred embodiments, the VLA-4 inhibitors have an $IC_{50}$ of less than about 500 nM, less than about 100 nM, and most preferably, less than about 50 nM. Applicants claimed methods and compounds enable those skilled in the art to predict and obtain VLA-4 inhibitors which have more desirable activities than those available in the art.

Applicants generated the claimed VLA-4 model as follows. A training set consisting of M16-01, M14, M18, M19 (FIGS. 3p, q, r and s respectively) was selected as representative of the different families of active, known, VLA-4 inhibitors. The training set was converted to multiconformer models with Catalyst™ 3.1 (Catalyst Tutorial Manual, MSI Inc., 16 New England Executive Park, Burlington, Mass. 01803) using the Best conformer generation process with energy set to 10 Kcal/molss and a maximum confs set to 250. These were used as input to the model generation program HIPHOP™ (HIPHOP Manual, MSI Inc., New England Executive Park, Burlington, Mass. 01803) as implemented in Catalyst™.

Applicants set the common features mode using the default arguments for all parameters except the following. All compounds were cited as principal by setting the principal column to 2 for each. The MaxOmit feature was set to 0. The spacing parameter was to 250 picometers, the max and min parameters were set to 9, and the number of returned models was set to 10. Applicants determined that Model 1 was representative of a VLA-4 inhibitor.

In order to further validate the claimed methods and model, applicants determined whether known VLA-4 inhibitors fit the claimed model. Protein X-ray crystallography, a powerful and commonly used experimental tool which provides structural insight into the biological conformation of macromolecules, was used to determine the crystallographic structure of vascular cell adhesion molecule 1 (VCAM ; Brookhaven Code 1 vca). This is a known physiological ligand of the VLA-4 receptor, which contains the sequence Ile-Asp-Ser. The Ile-Asp-Ser sequence is homologous to the Leu-Asp-Val sequence from CS1 upon which the peptidomimetics used in the claimed model were based. Peptides based upon Leu-Asp-Val region have been shown to inhibit the VLA-4-VCAM interaction. (Wang et al., 1995). Thus, applicants hypothesized that VLA-4 antagonists, when they bind to VLA-4, may mimic the structure of the Ile-Asp-Ser region of the VCAM structure.

The overlay between the model and Ile-Asp-Ser portion of VCAM is shown in FIG. 2. As can be seen in FIG. 2, the Ile "maps" the hydrophobic feature HYD3 and the carboxyl group of the Asp "maps" the negative ionizable feature NEG. Additionally, the carbonyl of the Ile residue maps to the hydrogen-bond acceptor feature. Thus applicants were able to confirm their claimed model by the mapping of the binding epitope of a known ligand of VLA-4 to the model.

ii) Model 2

Figure 4A:
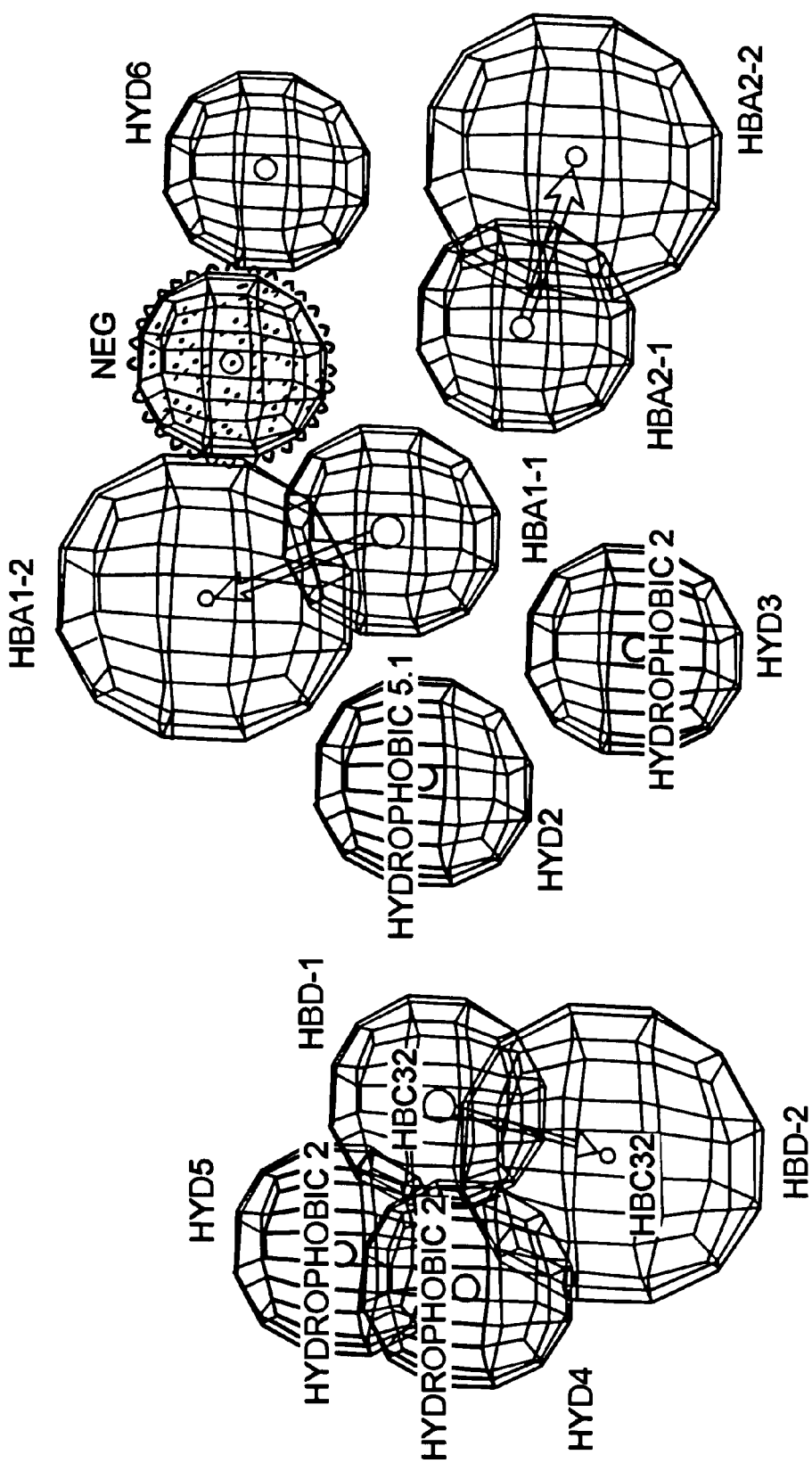
FIGS. 4(A) and (B). The overlay as computed by Catalyst between M2 and the claimed VLA-4 Model 2.
Figure 4B:
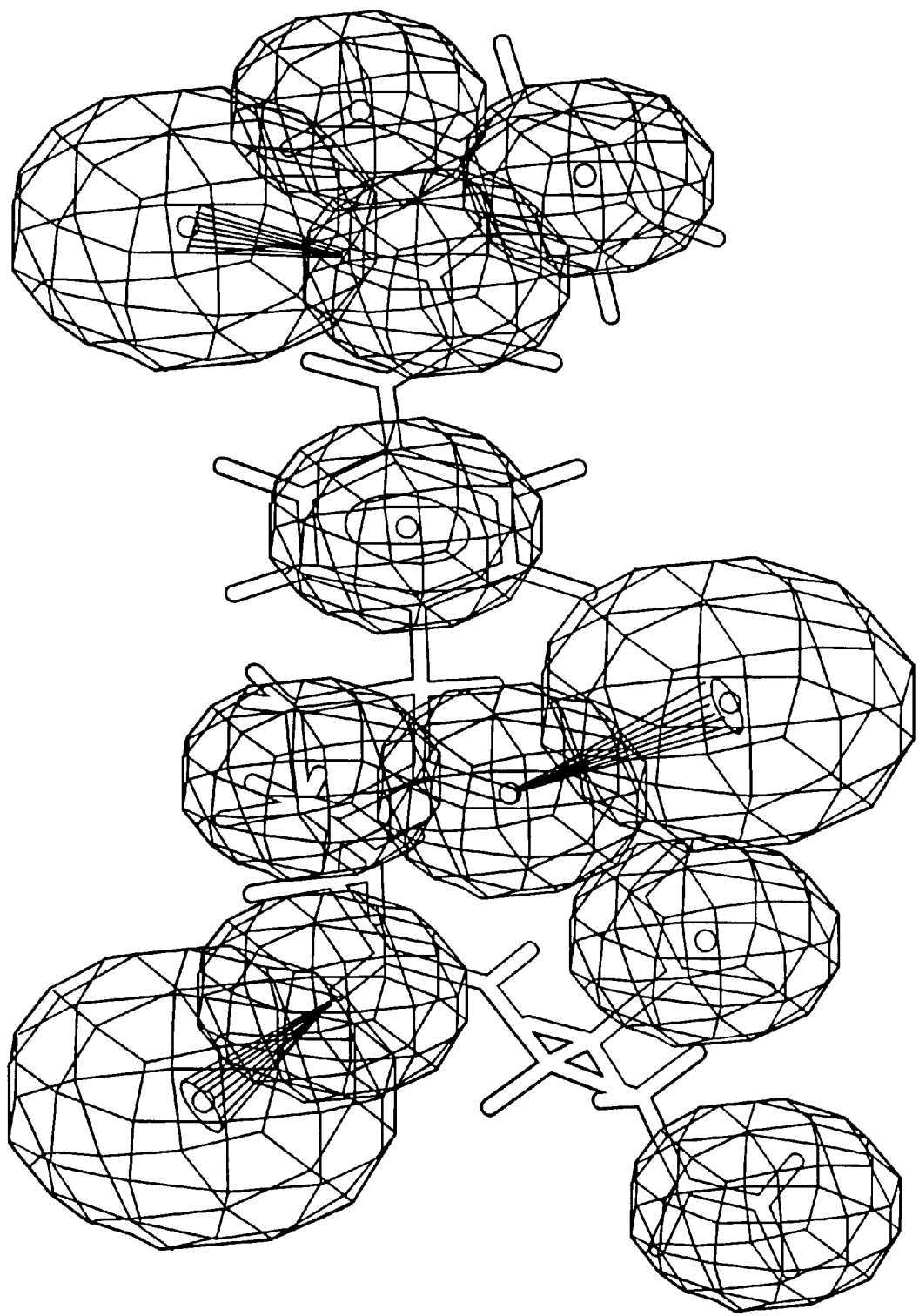
Figure 5A:
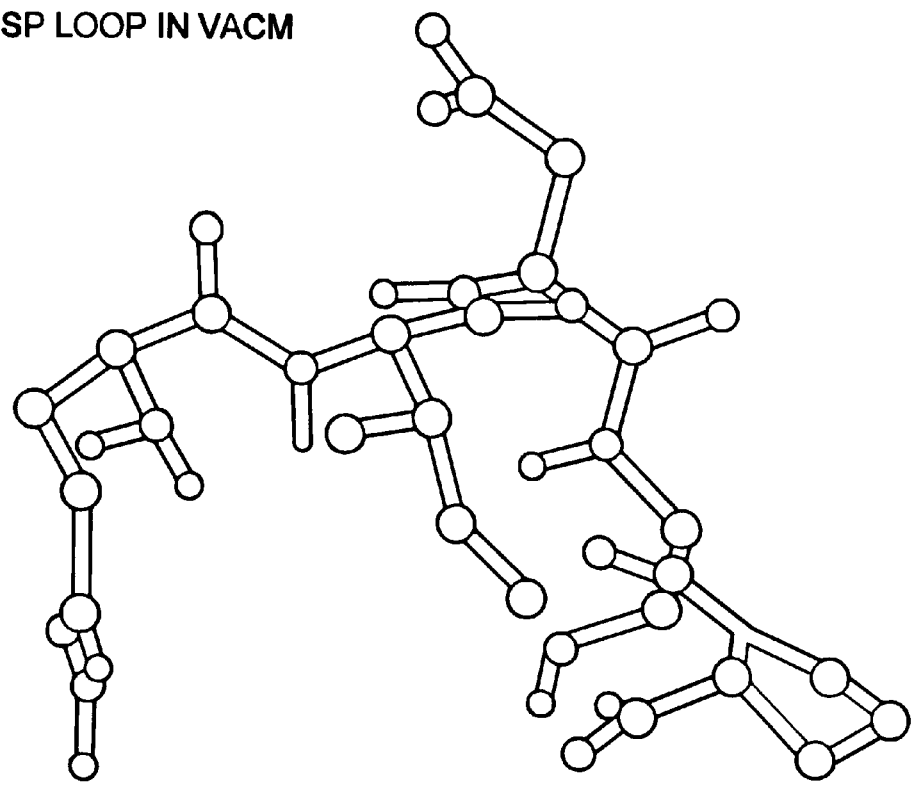
FIGS. 5(A) and (B). The correspondence of Model 3 and Gln-Ile-Asp-Ser-Pro region (residues 38–42) of the VCAM structure (Bernstein, F., 1977, "The Protein Databank: a computer-based archival for macromolecular structures," J. Mol. Biol., 112, 535–542; Brookhaven Code 1 VCA).
Figure 5B:
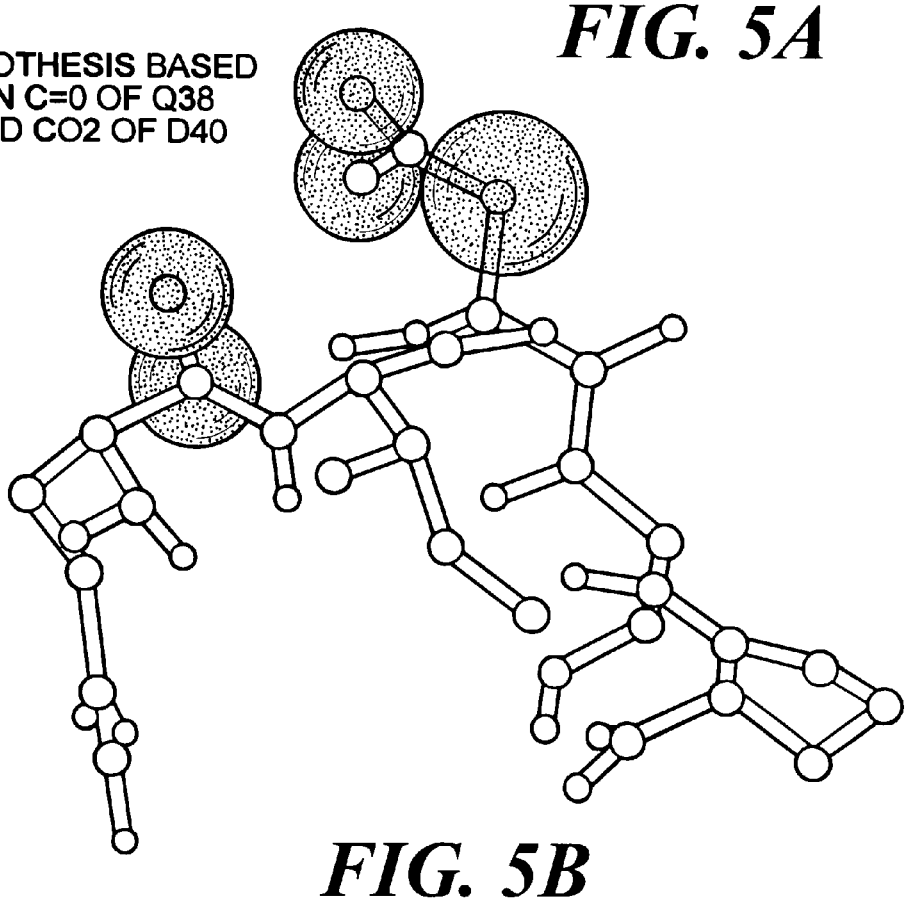

The claimed Model 2, depicted in FIG. 4, comprises features defined by the following tolerances and three dimensional coordinates. Specifically, Model 2 comprises the feature NEG ("N") and at least four other features selected from the remaining group of eight features.

Description of Model 2

| | Feature | x (Å) | y (Å) | z (Å) | tolerance (Å) |
|---|---|---|---|---|---|
| N | NEG | 5.19 | 2.48 | −0.84 | −1.5 |
| 1 | HBA1-1 | 2.625 | 0.078 | −0.451 | 1.5 |
| | HBA1-2 | 1.434 | 2.840 | −0.448 | 1.5 |
| 2 | HBA2-1 | 6.038 | −1.968 | −0.039 | 1.5 |
| | HBA2-2 | 8.314 | −2.560 | 1.832 | 1.5 |
| 3 | HBD-1 | −6.17 | −0.82 | 0.767 | 1.5 |
| | HBD-2 | −6.606 | −3.3 | 2.412 | 1.5 |
| 4 | HYD2 | −1.126 | −0.54 | 1.532 | 1.5 |
| 5 | HYD3 | 1.054 | −3.780 | −2.528 | 1.5 |

-continued

| Feature | x (Å) | y (Å) | z (Å) | tolerance (Å) |
|---|---|---|---|---|
| 6 HYD4 | −8.786 | −1.3 | 1.972 | 1.5 |
| 7 HYD5 | −8.786 | −0.580 | −0.788 | 1.5 |
| 8 HYD6 | 8.594 | 2.12 | −3.428 | 1.5 |

Model 2 was generated as follows. A training set consisting of M21, M26, M23, M22, and M24, was selected, and used to build Model 2.

The training set was converted to multiconformer models with Catalyst™ 2.3.1 (Catalyst Tutorial Manual, Release 2.3, MSI Inc., 16 New England Executive park, Burlington, Mass. 01803) using the Best conformer generation process with energy set to 15 Kcal/molss and a maximum confs set to 255. These were used as input to the hypothesis generation program HIPHOP™ (Catalyst Tutorial Manual, Release 2.3, MSI Inc., 16 New England Executive Park, Burlington, Mass. 01803) as implemented in Catalyst™ 2.3.1.

Hypothesis generation was carried out with the common features mode set to using the default arguments for all parameters except the following. All compounds were cited as principal by setting the principal column to 2 for each. M21 was not permitted to miss any features, M20 was allowed to miss up to two features, and all other compounds were permitted to miss up to one feature of any generated hypothesis by setting the MaxOmitFeatures columns to 0,2 and 1 respectively. The spacing parameter was set to 250 picometers, the max and min parameters were set to 9, and the number of returned hypothesis was set to 20. Applicants thus created 12 nine-featured models of which the fourth highest ranking was determined to best correlate the observed structure-activity data.

iii) Model 3

Applicants claimed Model 3 is based upon the discovery that certain VLA-4 inhibitors may be involved in coordinating to a metal in the VLA-4 ligands. Thus, applicants hypothesized that scaffolds which can coordinate to the metal may be useful to replace the scaffold of known VLA-4 inhibitors. The term "scaffold" is used herein to describe a portion of the chemical structure of VLA-4 inhibitors relating to the Leu-Asp-Val portion of known VLA-4 inhibitors. Applicants have discovered that the scaffold on known inhibitors can be replaced with new or different chemical substructures, thereby creating novel VLA-4 inhibitors.

Applicants based the claimed Model 3 upon VCAM, a known VLA-4 ligand, which was used to search for scaffolds which can coordinate to metals. The elements of Model 3, defined below, correspond to specific atom types, whereas Models 1 and 2 refer to chemical features.

Model 3 comprises the following five features:

| Feature | x (Å) | y (Å) | z (Å) | tolerance (Å) |
|---|---|---|---|---|
| Carboxyl C | −3.131 | −2.023 | 2.824 | 1.2 |
| Carboxyl O1 | −3.513 | −0.027 | 4.108 | 0.9 |
| Carboxyl O2 | −1.487 | −0.895 | 4.167 | 0.9 |
| Carbonyl C | −2.241 | 2.730 | 0.315 | 0.9 |
| Carbonyl O | −3.067 | 3.241 | 1.064 | 0.9 |

Applicants generated Model 3 by first defining key moieties of VCAM, a known VLA-4 ligand, which interact with metals. The backbone carbonyl group of residue Gln38 and the carboxyl group of Asp40 were identified. Applicants extracted the three-dimensional coordinates of the atoms included in the two moieties from the VCAM structure (Brookhaven Code 1VCA), and the then translated the two moieties into a searchable model using the Catalyst program.

B. Methods Using Claimed Models

The model of the invention provides those skilled in the art with a tool for discovering novel VLA-4 inhibitors, and thus, can be used to evaluate compounds prior to synthesis as to their ability to inhibit ligand binding to the VLA-4 receptor, or to design new compounds. The compounds being evaluated for VLA-4 inhibitory activity are referred to herein as "experimental compounds".

The VLA-4 models can be used to evaluate the ability of a compound to inhibit VLA-4. The compound evaluated for inhibitory activity, the "experimental compound" can be a novel structure designed using the claimed model, or, alternatively, can be a structure known in the art. Using the claimed models and methods, and the teachings herein, those skilled in the art can predict that an experimental compound which "fits" or "maps" to the models will have VLA-4 inhibitory activity.

In practice, the claimed models can be used in a variety of ways. For example, the claimed models can be used according to the claimed methods to identify novel VLA-4 inhibitors. First, one identifies an experimental compound to be evaluated for VLA-4 activity. This can be done for example, by searching a chemical database, or by modifying an existing compound. Alternatively, one can create a novel experimental compound. Those skilled in the art routinely utilize computer databases for searching, and computationally creating and/or modifying compounds and building compounds deNovo (e.g. LeapFrog "Ligand-Based Design Manual", Tripos Inc., 1699 S. Hanley Road, St. Louis, Mo. 63144-2913).

After identifying an experimental compound to be evaluated for VLA-4 inhibitory activity, the three dimensional structure of the experimental compound is determined. One can use computer programs such as, for example, Catalyst™ software, however, one is not limited to this software. By way of example, the compound can be drawn using the drawing tools in Catalyst™ and three-dimensional conformations can then be generated using, for example, the Best conformer generation process with energy set to 10 kcal/mols and the maximum number of conformations generated being set to 250. The experimental compound is then fit to the models using tools which can compare the two structures, such as, for example, Compare within the ViewHypothesis workbench.

The "fit" can be calculated automatically, for example, by determining if the compound can map to the chemical features in the models. This is dependent on whether the compound has the necessary or desired functional groups, and also whether they can adopt the necessary three dimensional arrangement to fit the model. The program can automatically report which features in the models are mapped by a compound.

If the experimental compound fits or maps any of the models, then one can experimentally determine whether that compound has the desired VLA-4 inhibitory activity by performing a direct binding assay (DBA). Those skilled in the art routinely perform such assays, and can readily determine the activity of the experimental compound.

In preferred embodiments, the claimed invention encompasses methods of identifying VLA-4 inhibitors having a commercially useful selectivity and potency. These values may vary widely, however, are easily determined by those skilled in the art based upon the desired application of the inhibitor. In general, the inhibitors of the invention have an $IC_{50}$ value of less than about 100 μm in a VLA-4 DBA. More preferably the claimed methods can be used to identify compounds having an $IC_{50}$ that value is less than about 50 μm, more preferably less than about 1 μm, In yet more preferred embodiments, the VLA-4 inhibitors have an $IC_{50}$ of less than about 500 nM, less than about 100 nM, and most preferably, less than about 50 nM. Applicants' claimed methods and compounds enable those skilled in the art to predict and obtain VLA-4 inhibitors which have more desirable activities than those available in the art.

A Method for the Discovery of DiphenylUrea Replacements in our VLA4 Inhibitors

Figure 3A:
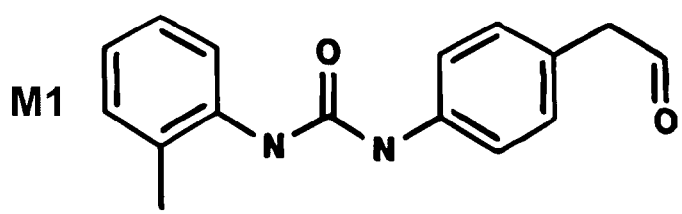
FIGS. 3(A)–(X). The chemical structure of compounds which map to the VLA-4 model 1.

A series of VLA-4 inhibitors previously reported, i.e. U.S. Ser. No. 08/376,372, comprise a diphenylurea "cap," and a "scaffold" as discussed above. The "cap" is used herein to describe a part of the chemical structure of VLA-4 inhibitors; generally, the cap on known inhibitors can be replaced with new or different chemical substructures, and thereby create novel VLA-4 inhibitors. The term cap is used herein to describe replacements of the N-terminal cap, i.e., 2'-tolylureidophenylacetyl (M1; FIG. 3a), with other chemical structures.

Applicants have invented methods of identifying mimetics of the diphenylurea cap of known VLA-4 inhibitors, which can be used to identify novel VLA-4 inhibitors. The claimed methods provide those skilled in the art with an effective and valuable tool to identify alternate cap structures, i.e. other than diphenyl analogs of diphenylurea, and hence can be useful for the identification of novel inhibitors.

The catShape program (Catalyst 3.1 Installation Guides and Release Notes, San Diego, Molecular Simulations Inc., 1996) is able to compare the shapes and volumes of compounds to each other. Applicants using the claimed methods, utilized this program to identify compounds that are similar to diphenylurea, (i.e. the "cap" on certain known VLA-4 inhibitors), and which are suitable for combinatorial chemistry.

The X-ray crystal structure of diphenylurea (Code name DPUREA) was extracted from the Cambridge Crystallographic Database (October 1991 release; Cambridge Crystallographic Data Center, 12 Union Road, Cambridge CB21EZ, U.K.). There are other diphenylurea containing compounds with very similar structures (FIG. 6) in the database (Code : PPESIR, KUHWHIT, SILVOY, GIMROJ10, GIMRUP10, GIMSAW10, SALTOW, SILTUC01). After converting the format of the file from Cambridge Database format to MDL SD format (MDL Information Systems, 14600 Catalina Street, San Leandro, Calif. 94577), the DPUREA it then used as input to the program catshape. This compound is used to search for compounds of similar shapes and volumes (FIG. 7) in a database of molecules (e.g., Available Chemical Directory; MDL Information Systems, 14600 Catalina Street, San Leandro, Calif. 94577). These chemical databases are converted into Catalyst databases by reading them into Catalyst 3.1 and building conformational models for each compound using the Fast conformer generation process with energy set to 10 kcal/mols, the maximum number of retries set to 100 and the maximum number of conformations set to 250. The catShape method involves calculating the size of the three principal orthogonal axis of each molecule in the database, together with the volume of the compound, and comparing each of these to that of the diphenylurea. The parameters are set to the default settings as described on page RN-10 of the Catalyst 3.1 Installation Guide and Release Notes (Molecular Simulations Inc., 1996, 9685 Scranton Road, San Diego). We used the default tolerances of 20% to the principal axes during the search procedure.

Thus, in certain embodiments the claimed invention encompasses methods for identifying mimetics of diphenylurea, specifically, methods of identifying non-related mimetics. The methods of the invention thus encompass methods of identify VLA-4 inhibitors having as a substructure a diphenylurea mimetic.

As discussed above, the methods of the invention involve as a first step the selection of an experimental compound to be evaluated for VLA-4 inhibitory activity, and determining whether said experimental compound contains a chemical substructure of similar shape and volume to diphenylurea as defined in the art, (i.e. by catshape or other programs). In certain embodiments, the method involves instead a determination of whether a three dimensional substructure of said experimental compound maps the features 2, 3, 5 and 6 in the VLA-4 Model 1. A three dimensional structure of the entire experimental compound is then obtained, either experimentally, or computationally, which is then mapped to the VLA-4 Model-1 Neg and feature 1. If the experimental compound has a substructure which contains an atom within about 0.5 to about 3 Å, more preferably about 1 to about 2 Å, and most preferably, about 2 Å of any of features 2, 3, 5 or 6, then the experimental compound is predicted to have VLA-4 inhibitory activity. The experimental compounds containing the urea mimetics (FIG. 8) can then be tested using a DBA, as discussed above.

Using the claimed three dimensional models those skilled in the art can identify both novel chemical entities which fit the model and have VLA-4 inhibitory activity, as well as identify known compounds having the desired activity which were not previously known to be VLA-4 inhibitors. The following examples further illustrate various embodiments of the claimed invention, and Further enable those skilled in the art to practice the invention.

C. Novel VLA-4 Inhibitors
(i) Inhibitors Which Map to Model 1

The claimed invention in certain broad embodiments encompasses novel compounds which have VLA-4 inhibitory activity. The claimed compounds fit the claimed models, have surprisingly good inhibitory activity and thus can be used, for example, in pharmaceutical preparations for treatment of diseases and conditions involving the VLA4 pathway.

Using the pharmacophore models and methods described in the foregoing sections, the applicants have discovered novel VLA4 inhibitors which fit the models.

For example, preferred embodiments encompasses VLA4 inhibitory compounds represented by GB-1:

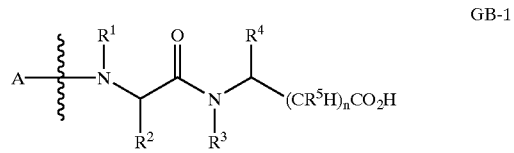

GB-1

A is selected from the group consisting of alkyl; aliphatic acyl optionally substituted with N-alkyl- or N-arylamido; aroyl; heterocycloyl; alkyl- or arylsulfonyl; aralkylcarbonyl optionally substituted with aryl; heterocycloalkylcarbonyl; alkoxycarbonyl; aralkyloxycarbonyl; cycloalkylcarbonyl optionally fused with aryl; heterocycloalkoxycarbonyl;

alkylaminocarbonyl; arylamino carbonyl and aralkylaminocarbonyl optionally substituted with bis(alkylsulfonyl) amino, alkoxycarbonylamino or alkenyl; alkylsulfonyl; aralkylsulfonyl; arylsulfonyl; cycloalkylsulfonyl optionally fused with aryl; heterocyclylsulfonyl; heterocyclylalkylsulfonyl; aralkoxycarbonyl; aryloxycarbonyl; cycloalkyloxycarbonyl; heterocyclyloxycarbonyl; heterocyclylalkoxycarbonyl; mono- or di-alkylaminocarbonyl optionally substituted with aryl; (alkyl)(aralkyl)aminocarbonyl; mono- or di-aralkylaminocarbonyl; mono- or di-arylaminocarbonyl; (aryl)(alkyl)aminocarbonyl; mono- or di-cycloalkylaminocarbonyl; heterocyclylaminocarbonyl; heterocyclylalkylaminocarbonyl; (alkyl)(heterocyclyl) aminocarbonyl; (alkyl)(heterocyclylalkyl)aminocarbonyl; (aralkyl)(heterocyclyl)aminocarbonyl; (aralkyl)(heterocyclylalkyl)aminocarbonyl; alkenoyl optionally substituted with aryl; alkenylsulfonyl optionally substituted with aryl; alkynoyl optionally substituted with aryl; alkynylsulfonyl optionally substituted with aryl; cycloalkenylcarbonyl; cycloalkenylsulfonyl; cycloalkylalkanoyl; cycloalkylalkylsulfonyl; arylaroyl, biarylsulfonyl; alkoxysulfonyl; aralkoxysulfonyl; alkylaminosulfonyl; aryloxysulfonyl; arylaminosulfonyl; N-arylurea-substituted alkanoyl; N-arylurea-substituted alkylsulfonyl; cycloalkenyl-substituted carbonyl; cycloalkenyl-substituted sulfonyl; alkenoxycarbonyl optionally substituted with aryl; alkenoxysulfonyl optionally substituted with aryl; alkynoxycarbonyl optionally substituted with aryl; alkynoxysulfonyl optionally substituted with aryl; alkenyl- or alkynylaminocarbonyl optionally substituted with aryl; alkenyl- or alkynyl-aminosulfonyl optionally substituted with aryl; acylamino-substituted alkanoyl; acylamino-substituted alkylsulfonyl; aminocarbonyl-substituted alkanoyl; carbamoyl-substituted alkanoyl; carbamoyl-substituted alkylsulfonyl; heterocyclylalkanoyl; heterocyclylaminosulfonyl; carboxyalkyl-substituted aralkoyl; carboxyalkyl-substituted aralkylsulfonyl; oxocarbocyclyl-fused aroyl; oxocarbocyclyl-fused arylsulfonyl; heterocyclylalkanoyl; N',N'-alkyl, arylhydrazinocarbonyl; aryloxy-substituted alkanoyl and heterocyclylalkylsulfonyl; alkenyl, alkynyl, cycloalkyl, aryl-fused cycloalkyl, cycloalkenyl, aryl, aryl-substituted alkyl ("aralkyl"), aryl-substituted alkenyl or alkynyl, cycloalkyl-substituted alkyl, cycloalkenyl-substituted cycloalkyl, biaryl, alkoxy, alkenoxy, alkynoxy, aryl-substituted alkoxy ("aralkoxy"), aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl;

n=1–4;

When $R^3$ is H, n=2–4; or when n=1, only $R^3$ or $R^5$ is H;

$R^1$ and $R^4$ are independently selected from the group consisting of H, alkyl, aryl, aralkyl; alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, carboxamide, amine, alkylsulfone, and alkylsulfoxide;

$R^2$ is selected from the group consisting of H, alkyl: alkyl optionally substituted with amine, cycloalkyl, alkylsulfone, and alkylsulfoxide;

$R^3$ is selected from the group consisting of H, alkyl, and alkyl optionally substituted with aralkoxy, hydroxy;

X is selected from the group consisting of —CH$_2$—, S, O, NR$^4$, NCOR$^7$, and NSO$_2$R$^7$;

m is 3 or 4;

p is 3 or 4;

q and r are independently 1 or 2;

$R^1$ and $R^2$ may be taken together to form —(CR$^1$R$^2$)$_p$—, or —(CR$^1$R$^2$)$_q$X (CR$^1$R$^2$)$_r$—;

$R^3$ and $R^4$ may be taken together to form —(CR$^1$R$^2$)$_m$— or —(CR$^1$R$^2$)$_q$X (CR$^1$R$^2$)$_r$—;

$R^3$ and $R^5$ may be taken together to form —(CR$^1$R$^2$)$_m$—;

$R^5$ is selected from the group consisting of H, hydroxy, alkyl, NH$_2$, NHSO$_2$R$^7$, NHCOR$^7$, and NHCO$_2$R$^7$;

$R^7$ is selected from the group consisting of alkyl; aryl; aralkyl; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, and carboxamide;

More preferred compounds are compounds M101–M112, M116, M117, M124, M125, M127–M129, M139, M140, M141–M150 in FIGS. 15-1–15-50.

In other embodiments, preferred compounds are represented by GB-2:

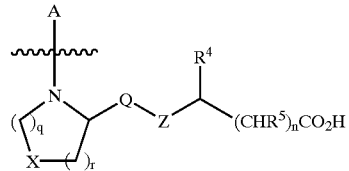

GB-2

A is the same as defined in GB-1;

Q is —CH$_2$—, —CH═CH—, or —CH$_2$CH$_2$—;

Z is selected from the group consisting of: —CHR$^4$—, —CO—, O, S, —SO$_2$—, NR$_4^4$, NCOR$^7$, NSO—R$^7$, —NCO$_2$R$^7$—, and —CONR$^7$—;

$R^4$ is selected from the group consisting of H, alkyl, aryl, aralkyl: alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, carboxamide, amine, alkylsulfone, or alkylsulfoxide;

$R^5$ is selected from the group consisting of H, hydroxy, alkyl, NH$_2$, NHSO$_2$R$^7$, and NHCOR$^7$;

$R^7$ is selected from the group of alkyl, aryl, aralkyl; alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide;

X is selected from the group consisting of —CH$_2$—, S, O, NR$^4$, NCOR$^7$, and NSO$_2$R$^7$;

n=0–5;

q and r are independently selected from 1, 2.

More preferred compounds are in FIG. 15-1–15-50, as are the most preferred compounds M115, M118–M123, M126, M130–M135, in FIG. 15-1–15-50.

The novel VLA-4 inhibitors claimed by Applicants map to the "Neg" feature of Model 1, and from 3–7 of features 1–7. The compounds of the invention preferably have an inhibitory activity in the range of about 100 μM to about 0.5 nM, preferably of less than about 50 μm, more preferably less than about 500 nM, and most preferably, less than about 50 nM.

Preferable inhibitors map to at least 3 of Features 1–7 of Model 1, and have an IC$_{50}$ value of less than about 50 nM. More preferable inhibitors map to at least 5 of Features 1–7.

ii) Inhibitors Which Map to Model 2

In other embodiments the claimed VLA-4 inhibitors map to the "Neg" feature of Model 2, and at least four other features selected from Features 1–8 of Model 2. More preferably, the inhibitors map to at least 6 features, and most preferably, at least 7 features, in addition to "Neg."

In most preferred embodiments, the claimed inhibitors which map to "Neg" and from 4 to 8 of Features 1–8 of Model 2, have an $IC_{50}$ value of about 50 μm to about 0.5 nM. The compounds of the invention preferably have an inhibitory activity in the range of about 100 μM to about 0.5 nM, preferably of less than about 50 μm, more preferably less than about 500 nM, and most preferably, less than about 50 nM.

The most preferable inhibitors map to at least 6 of the Feature of Model 2, and have an $IC_{50}$ value of less than about 50 nM.

iii) Inhibitors Which Map to Model 3

In yet other embodiments, the claimed compounds comprise a scaffold which map to Model 3. Applicants have discovered that compounds comprising those scaffolds have excellent inhibitory activity ranging from about 500 μm to about 0.5 nM. The compounds of the invention preferably have an inhibitory activity in the range of about 100 μM to about 0.5 nM, preferably of less than about 50 μm, more preferably less than about 500 nM, and most preferably, less than about 50 nM.

Those skilled in the art will recognize that inhibitors of the invention may map to more than one of the claimed Models.

EXAMPLES

Example 1

Fit of Claimed Models to the Experimental Structure of a Known VLA-4 Ligand

In order to further validate the claimed methods and model, applicants determined whether known VLA-4 inhibitors fit the claimed Model 1. Protein X-ray crystallography is a powerful and commonly used experimental tool to provide structural insight into the biological conformation of macromolecules, and was used to determine the crystallographic structure of vascular cell adhesion molecule 1 (VCAM ; Brookhaven Code 1vca). This is a known physiological ligand of the VLA-4 receptor, which contains the sequence Ile-Asp-Ser. The Ile-Asp-Ser sequence is homologous to the Leu-Asp-Val sequence from CS1 upon which the peptidomimetics used in the claimed model were based. Peptides based upon Leu-Asp-Val region have been shown to inhibit the VLA-4-VCAM interaction. Thus, applicants hypothesized that VLA-4 antagonists, when they bind to VLA-4, may mimic the structure of the Ile-Asp-Ser region of the VCAM structure.

Figure 9:
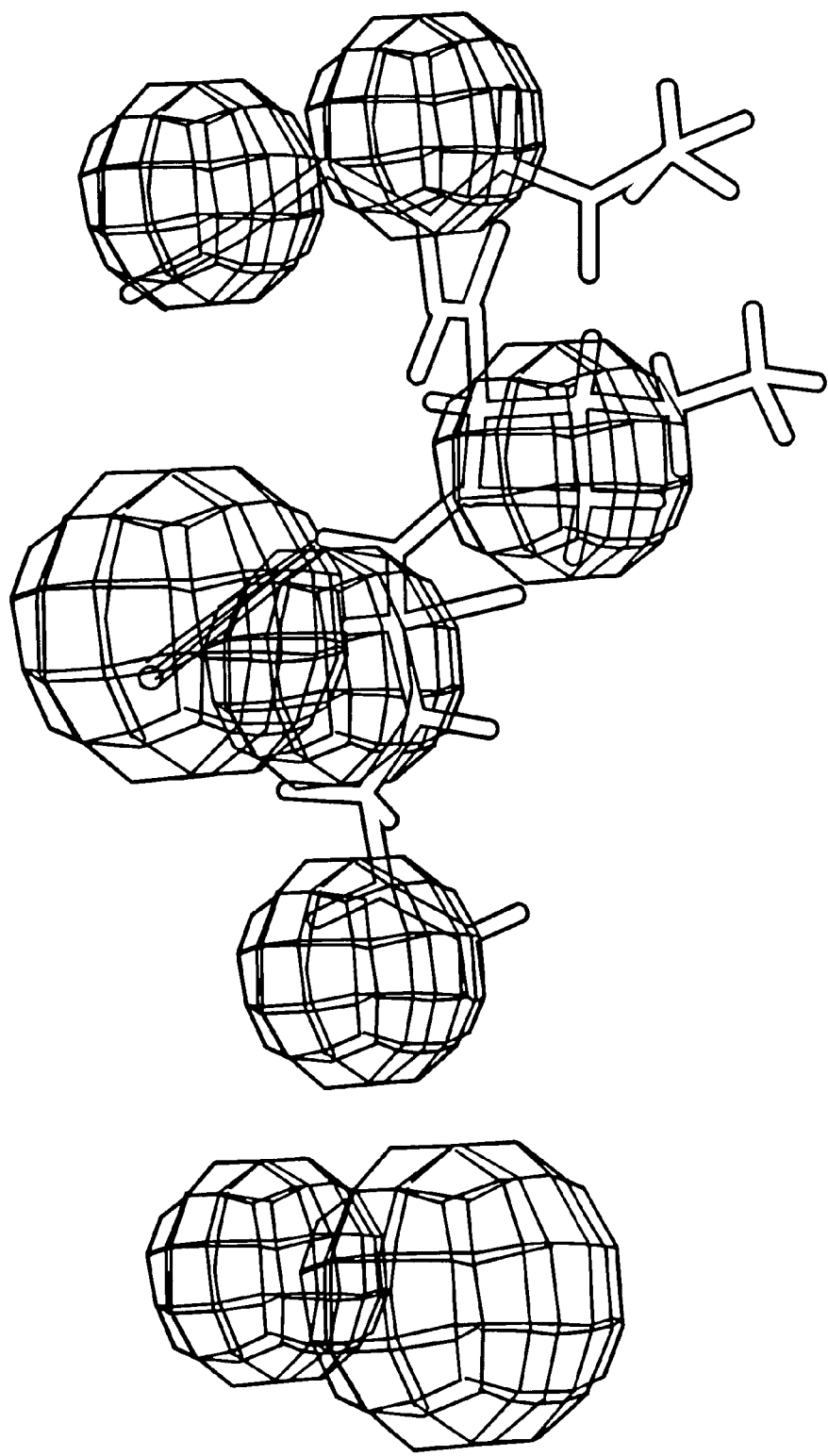
FIG. 9. The overlay of the Gln-Ile-Asp-Ser-Pro SEQ ID NO.5 portion of the VCAM X-ray structure (Residue Number 38–41) and a truncated version of the VLA-4 model 1

The overlay between the model and Ile-Asp-Ser portion of VCAM is shown in FIG. 9. As can be seen in FIG. 9, the Ile "maps" to the hydrophobic feature HYD3 and the carboxyl group of the Asp "maps" to the negative ionizable feature NEG.

Additionally, the carbonyl of the Ile residue maps to the hydrogen-bond acceptor feature HBA (Note that HBA describes the feature HBA-1 and HBA-2). Thus, applicants were able to confirm their claimed model by the mapping of the binding epitope of a known ligand of VLA-4 to the Model-1.

Example 2

How the Models Fit Different Chemical Templates

Figure 3B:
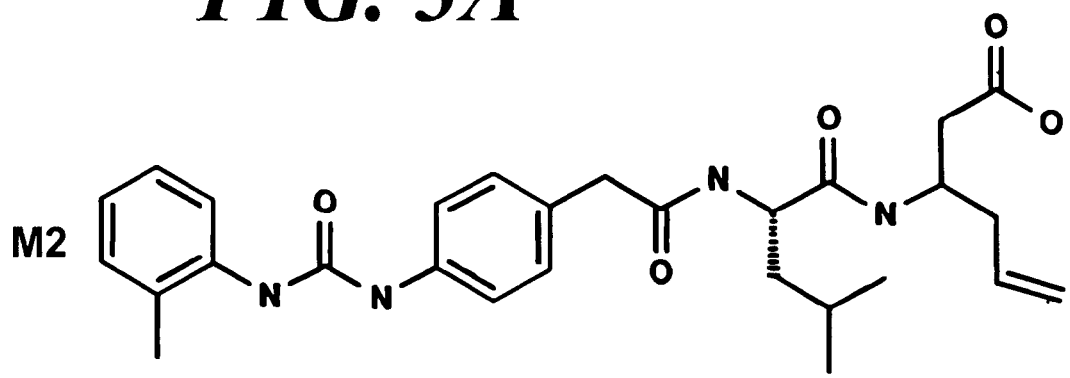
Figure 3C:
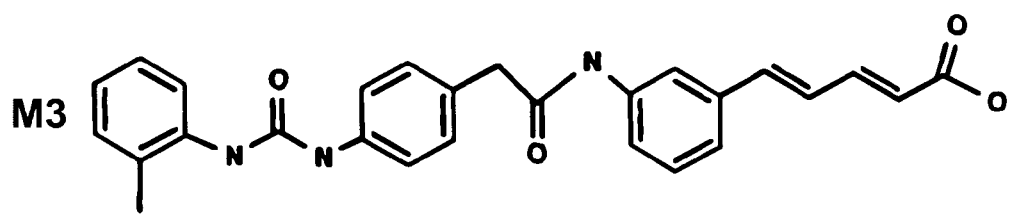
Figure 3D:
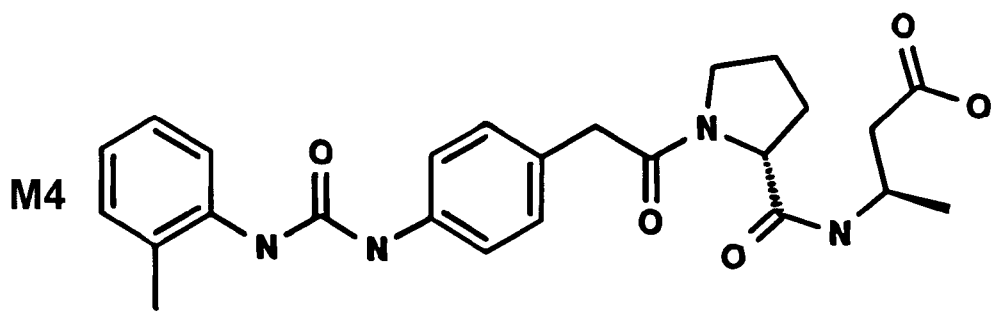
Figure 3E:
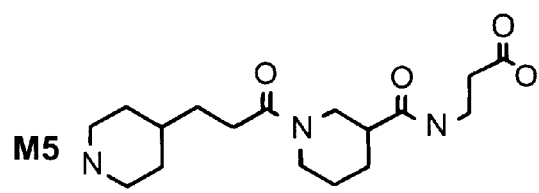
Figure 3F:
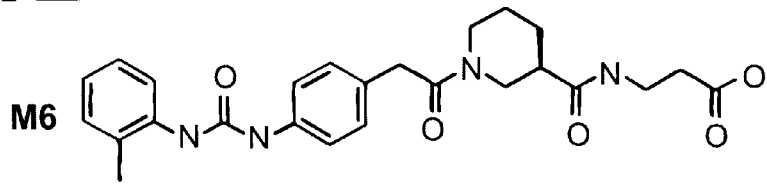
Figure 10:
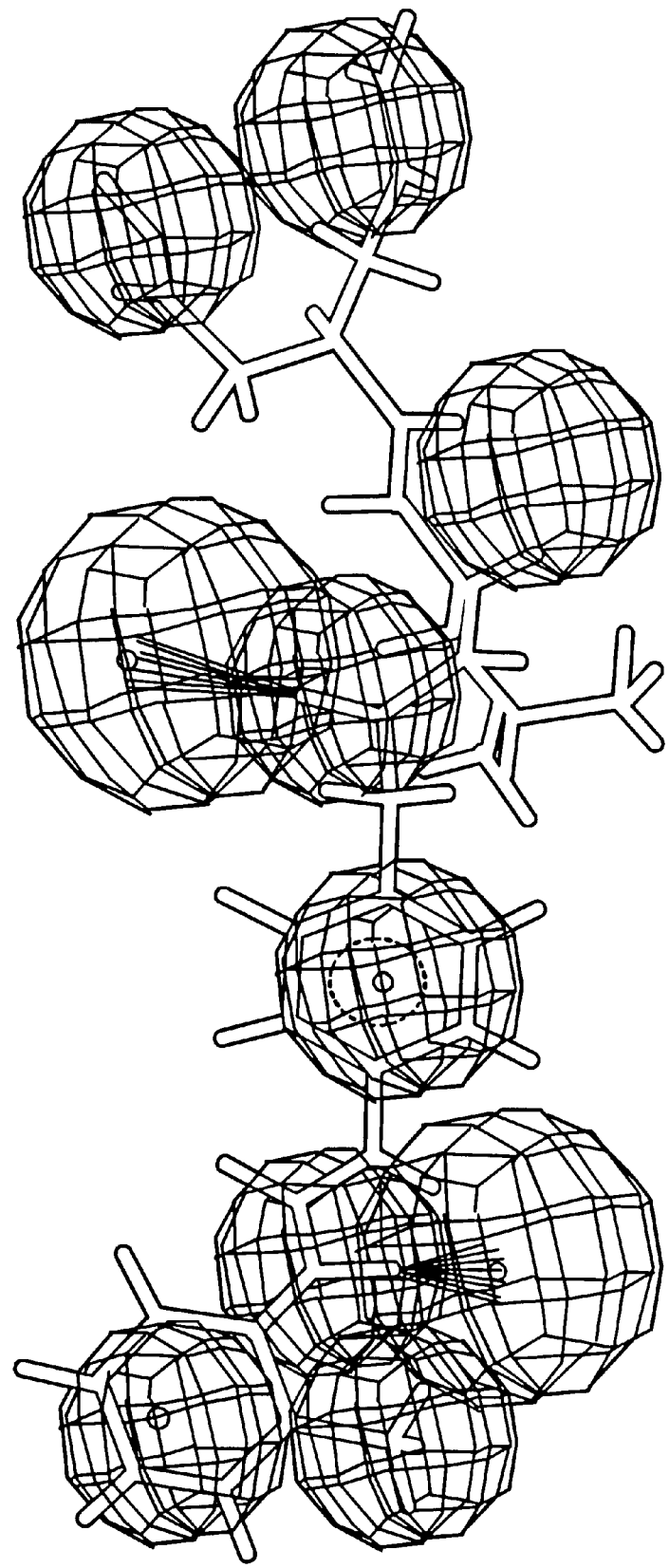
FIG. 10. The overlay, as computed by Catalyst, between M2 and the VLA-4 model 1.
Figure 11A:
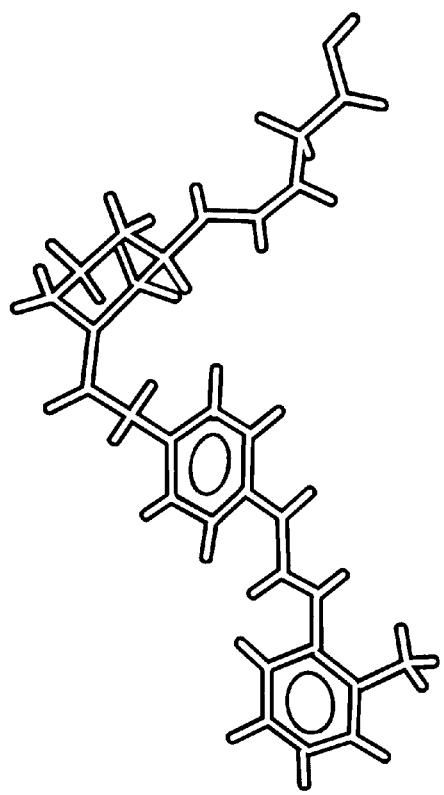
FIGS. 11(A) and (B). The conversion of the compound M5 into M6, a VLA-4 inhibitor. The overlay of M6 with the VLA-4 model 1 is shown.
Figure 11B:
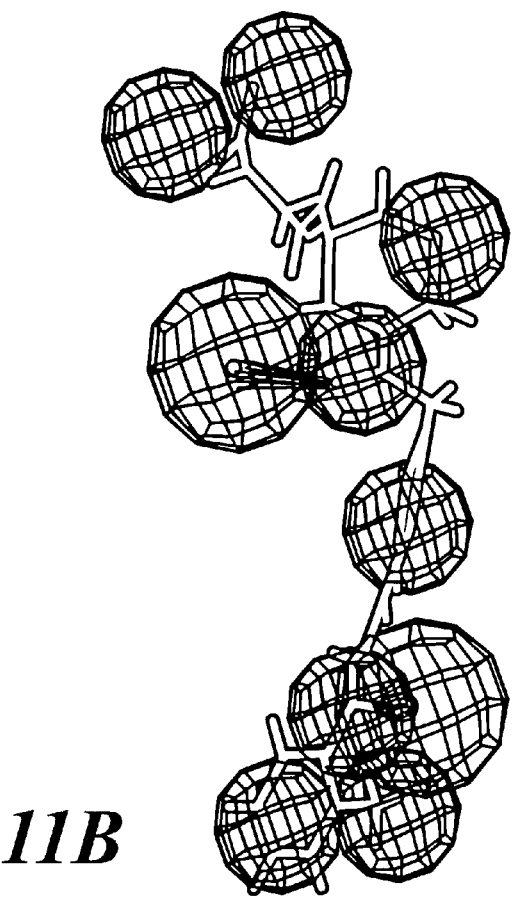

In order to further validate the claimed model 1, applicants investigated its ability to fit known VLA-4 inhibitors which were not used in the construction of the model, and were not synthesized with any knowledge of the model. Model 1's ability to map M2, M3 and M2(FIG. 3b, c and d respectively) was determined. The scaffolds of these three molecules are structurally quite different, yet each maps to the claimed model 1. Thus, applicants were able to confirm that the claimed model 1 can, in fact, be used to identify VLA-4 inhibitors, and to identify alternative chemical templates (FIG. 10; see method 1c for definition of fit).

Example 3

Replacement of -Leu-Asp-Val- Portion of Known VLA-4 Inhibitors with Other Scaffolds Applicants used the claimed models and methods to design alternative scaffolds to replace -LDV- portion of known VLA4 inhibitors. One such example is illustrated by M6 which fits the models. This novel compound was determined to be a potent VLA4 inhibitor in a direct binding assay with an $IC_{50}$ of 800 nM.

Example 4

Replacement of the Diphenylurea Portion of known VLA-4 Inhibitors

Figure 3G:
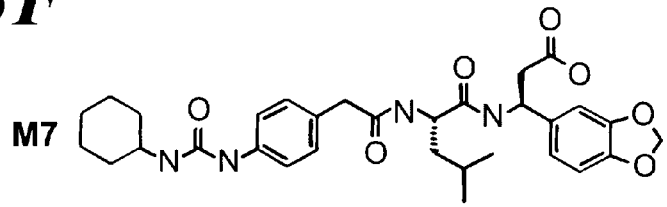
Figure 3H:
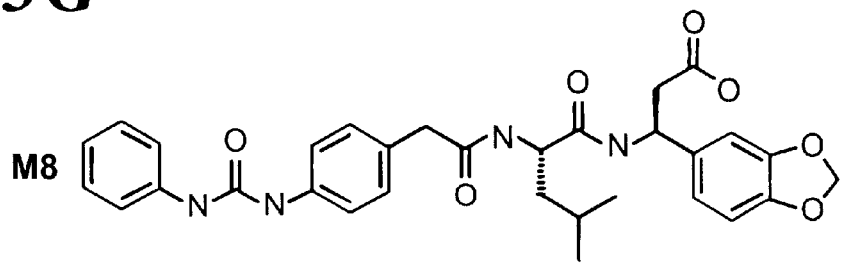
Figure 6:
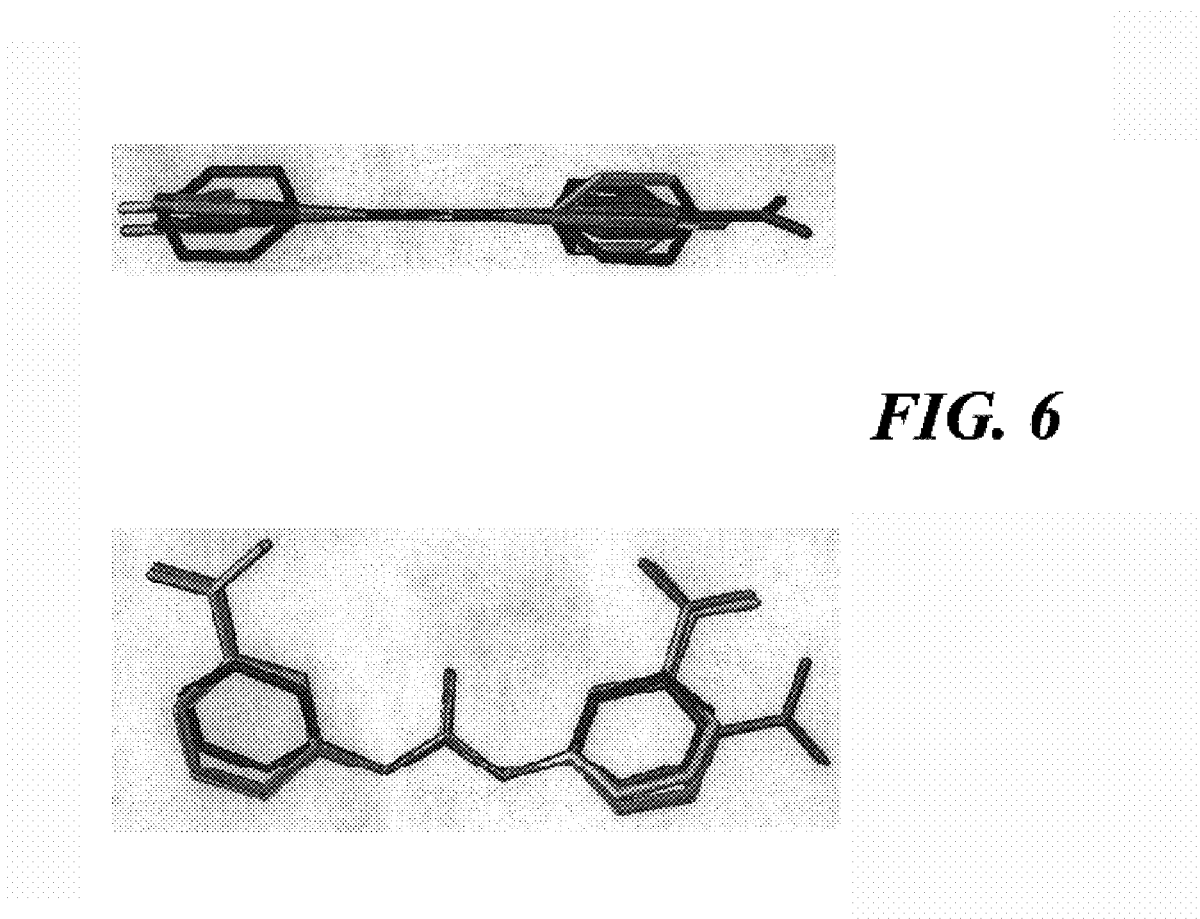
FIG. 6. Overlay of diphenylurea containing compounds from the Cambridge Crystallographic Database (Code names PPESIR, KUHWHIT, SILVOY, GIMROJ10, GIMRUP10, GIMSAW10, SALTOW, SILTUC01). (Cambridge Crystallographic Data Center, 12 Union Road, Cambridge, CB21EZ, U.K.) A top view and end-on-view of the overlaid compounds are shown.
Figure 7:
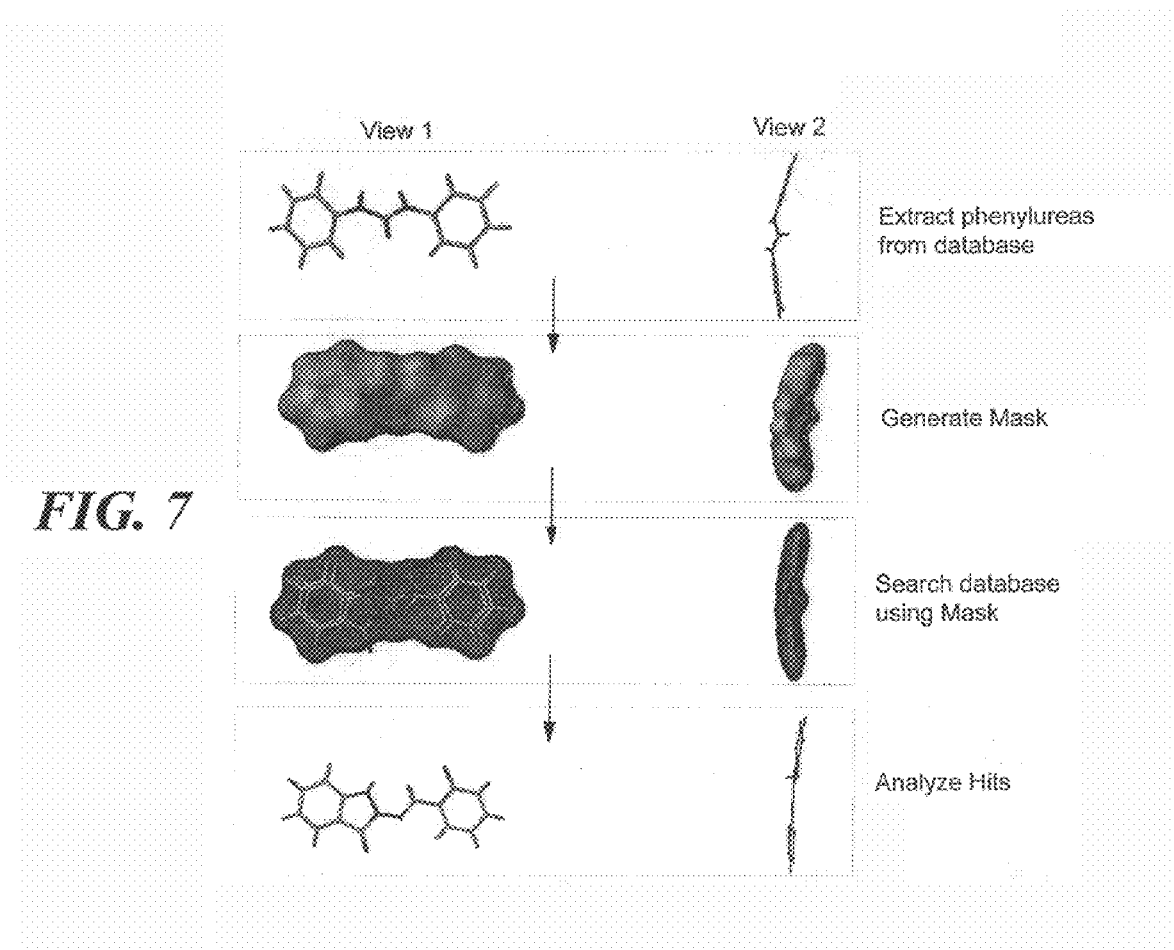
FIG. 7. A schematic representation of our search procedure for identifying diphenylurea mimetics. This involves defining and extracting the compound DPUREA from the Cambridge crystallographic database, and defining its shape using the program catshape. This is defined in terms of a mask which represents the 3 principal axes of the molecule and its volume. This mask is then used to search for other molecules in a Catalyst database with similar shapes and volumes.
Figure 8A:
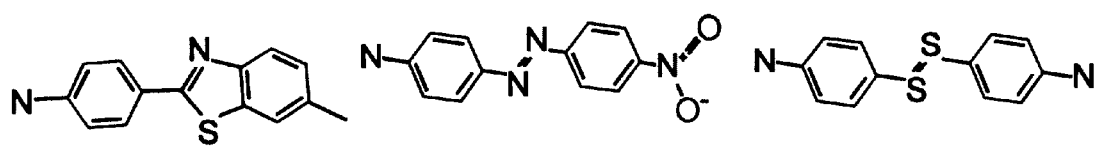
FIGS. 8(A) and (B). Examples of diphenylurea mimetics extracted from a multiconformational database of amine containing caps extracted from the ACD.
Figure 8A:
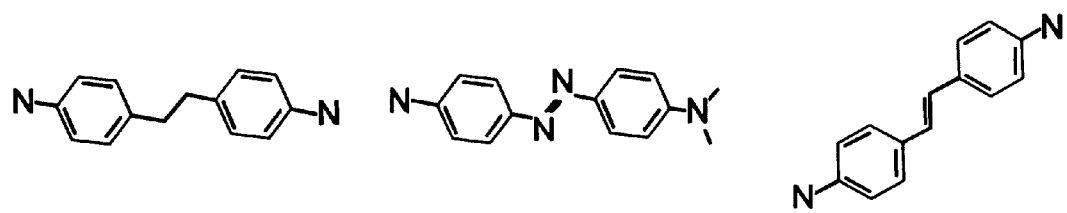
Figure 8A:
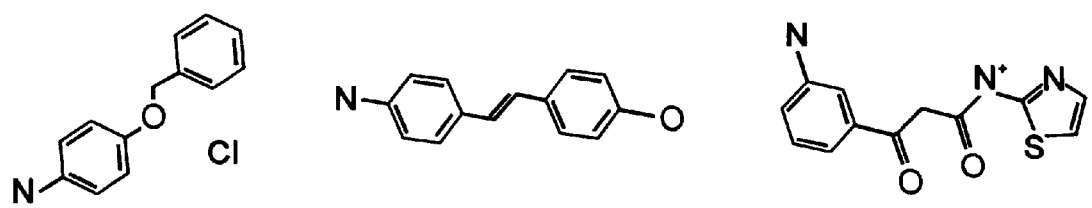
Figure 8A:
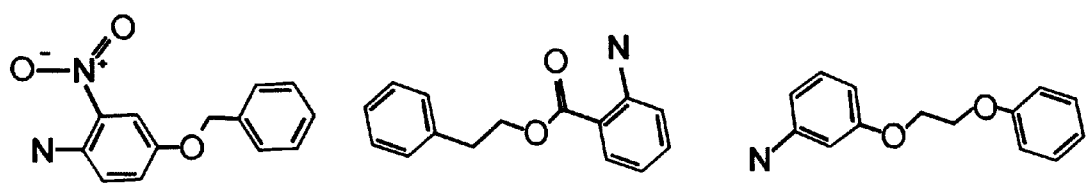
Figure 8A:
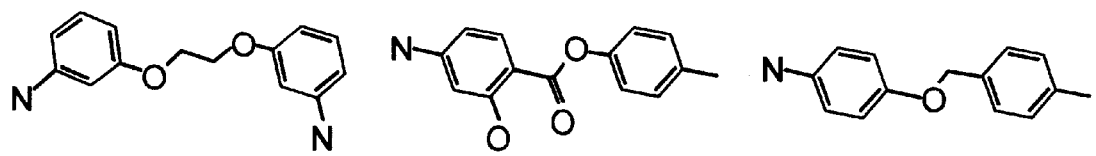
Figure 8B:
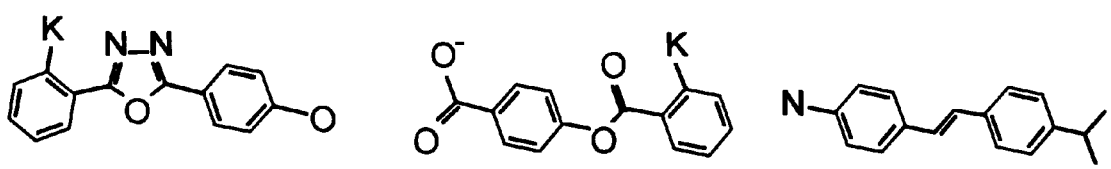
Figure 8B:
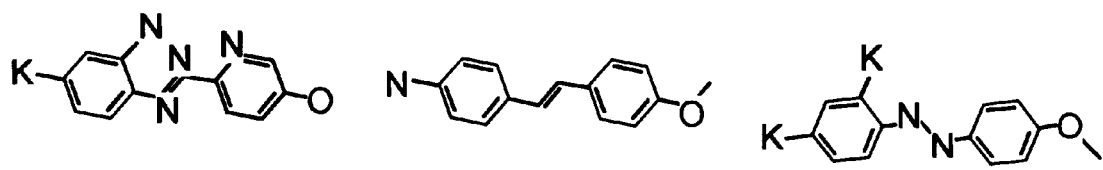
Figure 8B:
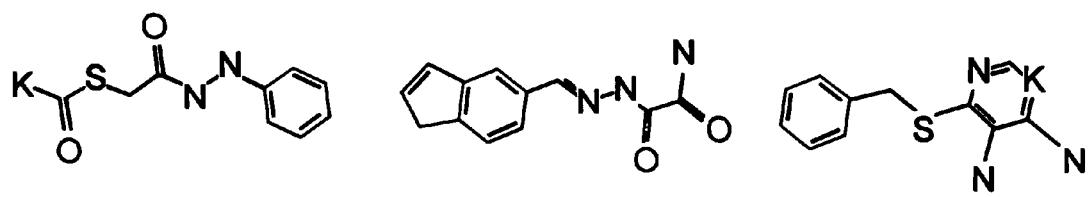
Figure 8B:
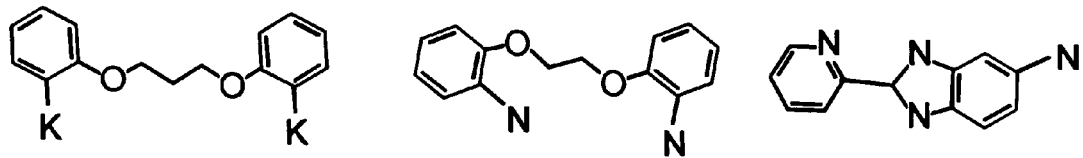
Figure 8B:
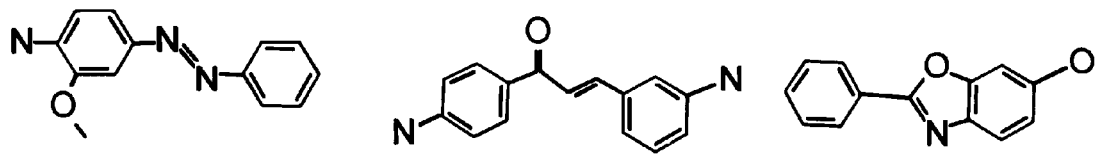

Applicants have used the claimed model 1 to identify mimetics of the diphenylurea portion of known VLA-4 inhibitors. The claimed model has two hydrophobic features (HYD2 and HYD5), which map to the two phenyl groups of the diphenylurea. Based upon the claimed model it was known that these features and the HYD4 and HBD were arranged in a plane. Analysis of the X-ray structures of diphenylurea shows them to adopt a planar arrangement between the two phenyl rings (FIG. 6). To further support the validity of the claimed model, data was obtained which showed that replacement of the phenyl with a non-planar cyclohexyl group (M7 ; FIG. 3g) (M8 ; FIG. 3h) diminishes binding (M7 $IC_{50}$ 10 μM, M8 $IC_{50}$ 50 nM), thus confirming the importance of planarity.

Figure 3I:
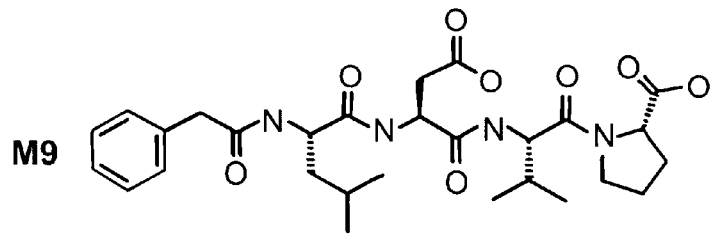
Figure 3J:
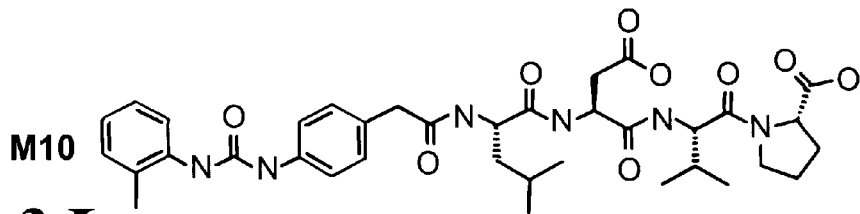

Additionally, applicants have shown that shorter molecules are weaker binders. Thus, for example, Phenylacetyl-Leu-Asp-Val-Pro (FIG. 3i) has an $IC_{50}$ of 2 μM, while oMePUPA-Leu-Asp-Val-Pro (FIG. 3j) has an $IC_{50}$ of 8 nM, confirming that the diphenylurea is occupying a cavity in which the length and shape of the molecule lead to high affinity binding.

Applicants searched for molecules with similar shapes and volumes to the diphenylurea model (FIG. 7) using the program catShape (Catalyst 3.1 Installation Guides and Release Notes, San Diego, Molecular Simulations Inc., 1996). FIG. 8 shows examples of search hits.

Figure 3K:
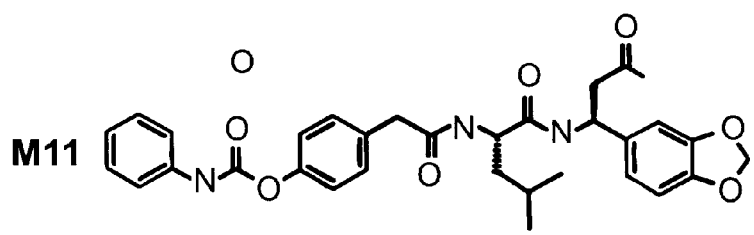
Figure 3L:
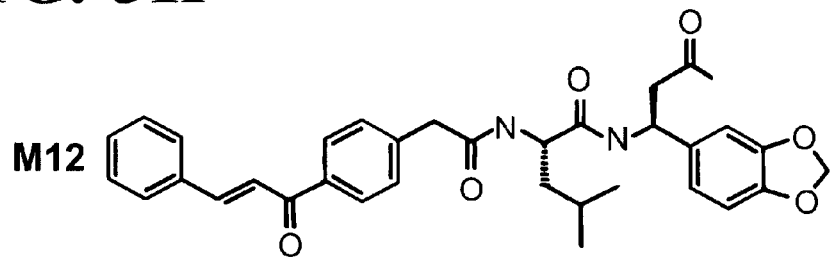

M11 (FIG. 3k) and M12(FIG. 3l) were synthesized, the diphenylurea was replaced with the substructure returned from the search. M11 and M12 had an $IC_{50}$ of 34 nM and 383 nM respectively. Thus, the claimed invention provides alternative caps which predict potent inhibitors of VLA-4.

Example 5

Figure 12:
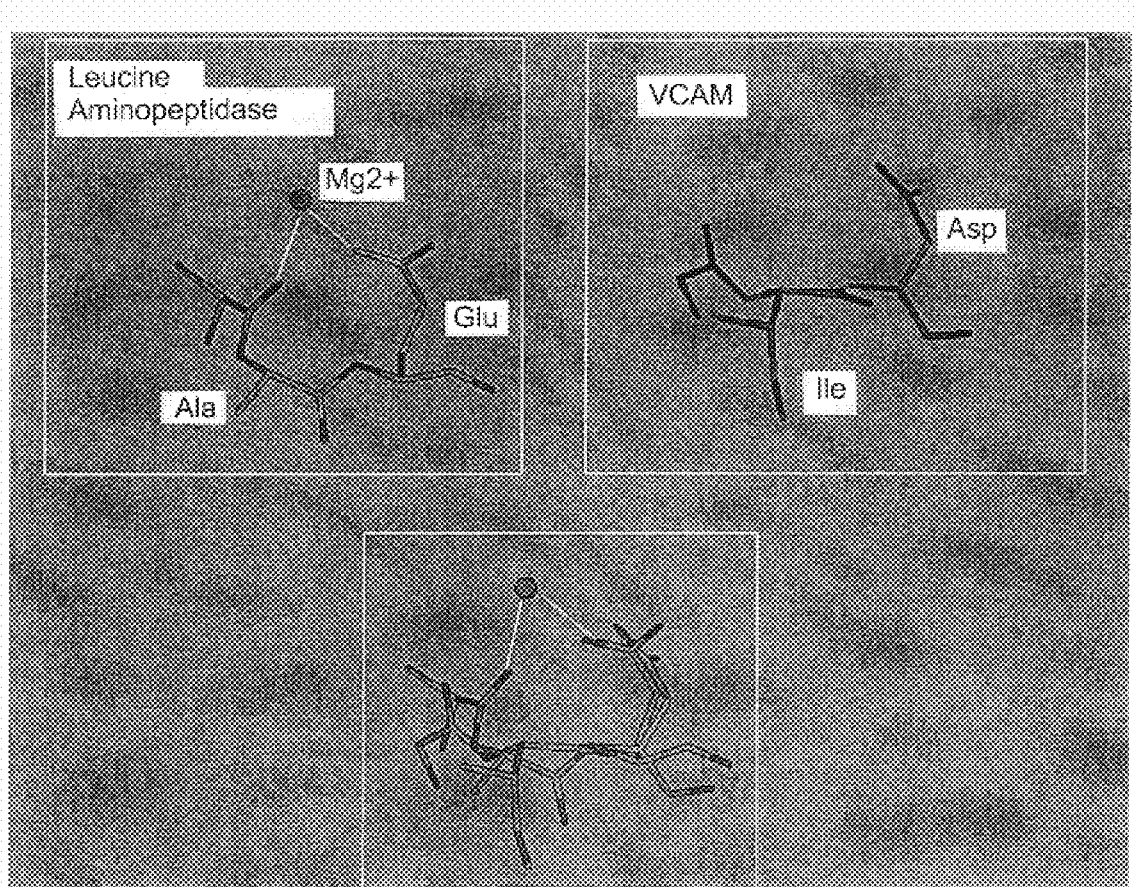
FIG. 12. Comparison of the X-ray structures of Leucine Aminopeptidase (Brookhaven Code 1BPM) and VCAM (Brookhaven Code 1VCA.)

Replacement of the Leu-Asp-Val Portion of Known Antagonists with Scaffolds that can Coordinate to a Metal The claimed invention teaches that desirable VLA-4 inhibitors are often involved in coordinating to a metal in the VLA-4 receptor. Therefore according to the claimed Model 3, scaffolds that can coordinate to the metal may be useful to replace the Leu-Asp-Val portion of VLA-4 antagonists. The evidence for the metal coordination of the VLA-4 antagonists includes structural and biological data.

i) All integrins require $Mg^{2+}$ for ligand binding(Springer, T A, Nature, 346, 425–433). This, together with the presence of Asp residues in the known VLA-4 receptor binding regions of Fibronectin(Leu-Asp-Val) and VCAM (Ile-Asp-Ser), suggested that the ligand coordinates to a metal.

ii) The applicants have discovered that the geometry of the hydrogen bond acceptor (HBA) and NEG feature in our model is consistent with the geometry of carboxyl groups and hydrogen-bond acceptors in molecules that coordinate to metals. For example, in FIG. 12 the $Mg^{2+}$ binding site of Leucine Aminopeptidase is shown. In this site, the carbonyl oxygen of residue i and the carboxyl side chain of residue i+2 are coordinated to the $Mg^{2+}$. This geometry of the carbonyl and carboxyl group is very similar to the geometry of the carbonyl group of Leu of residue i and the Asp carboxyl at i+2 in M2 (FIG. 3b) when fitted to Model 1. In addition, the crystal structure of the Ile-Asp-Ser portion of VCAM, a known ligand to VLA-4, shows that the geometry of the carbonyl oxygen of the Ile at position i and the carboxyl of the Asp at i+2 are similar to the geometry of known metal binding proteins (see FIG. 12) and also to model 1.

Figure 3M:
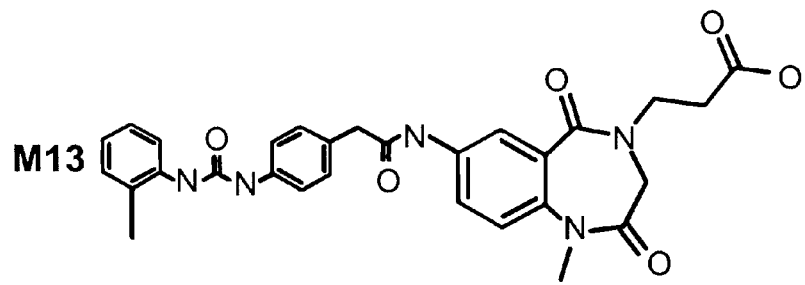
Figure 3N:
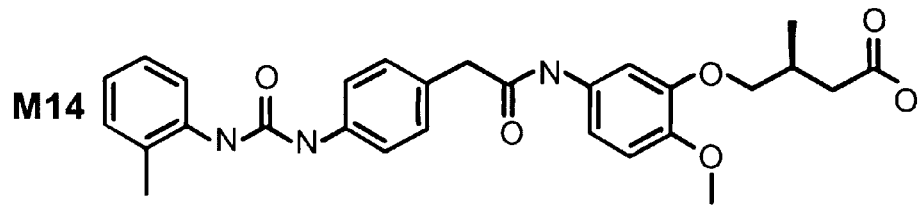
Figure 3O:
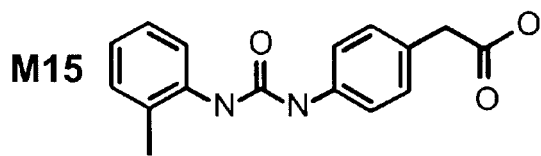
Figure 3P:
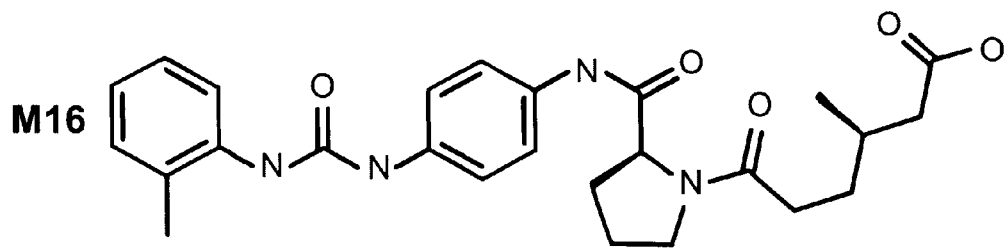
Figure 3Q:
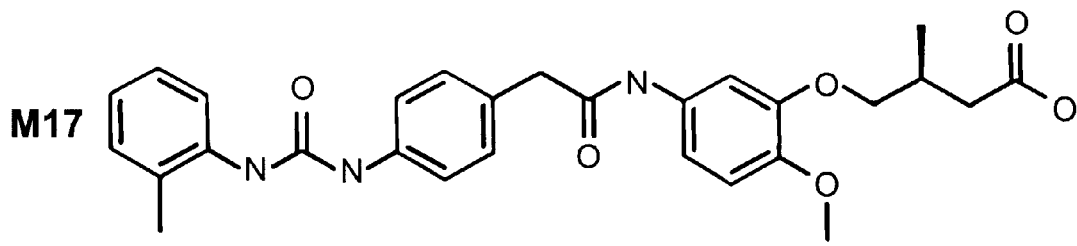
Figure 3R:
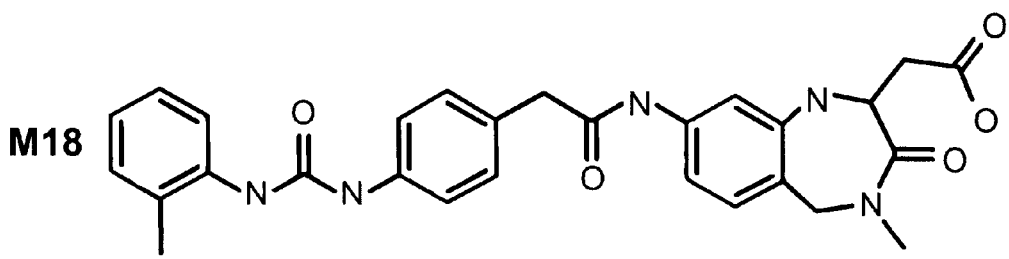
Figure 3S:
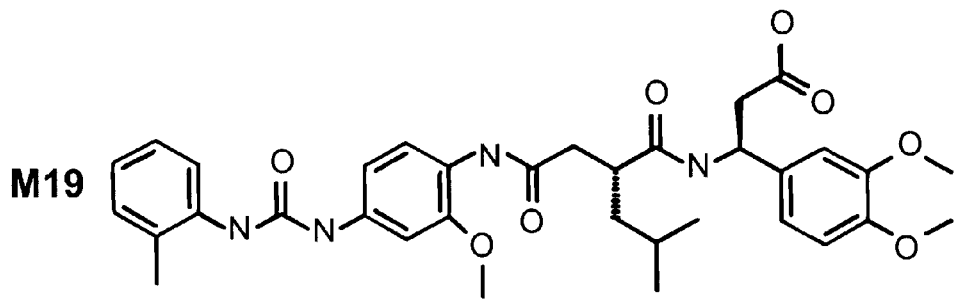
Figure 3T:
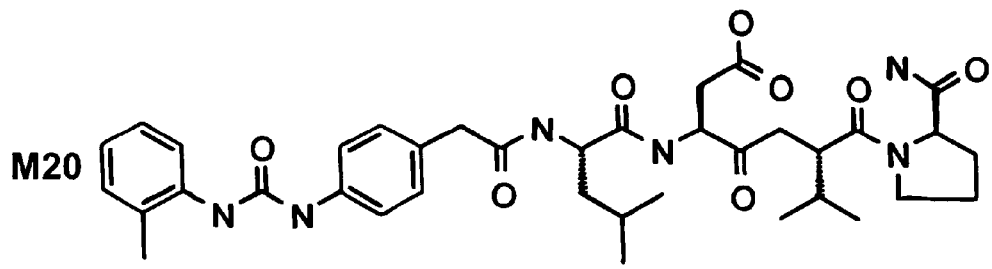
Figure 3U:
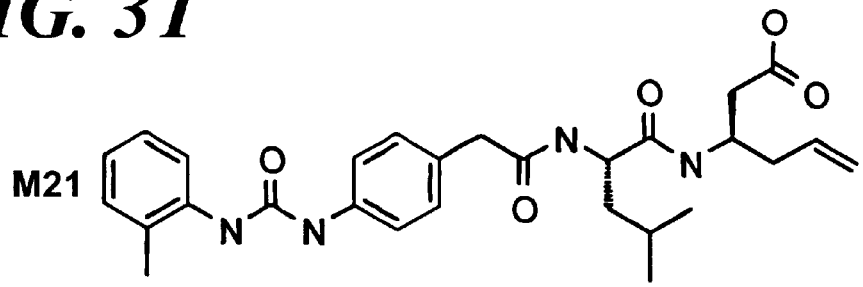
Figure 3V:
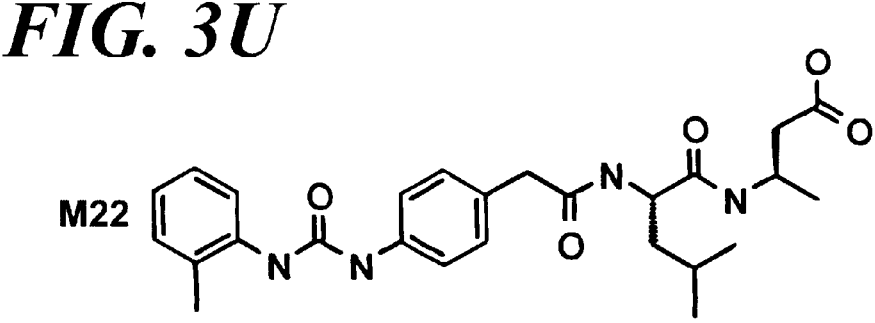
Figure 3W:
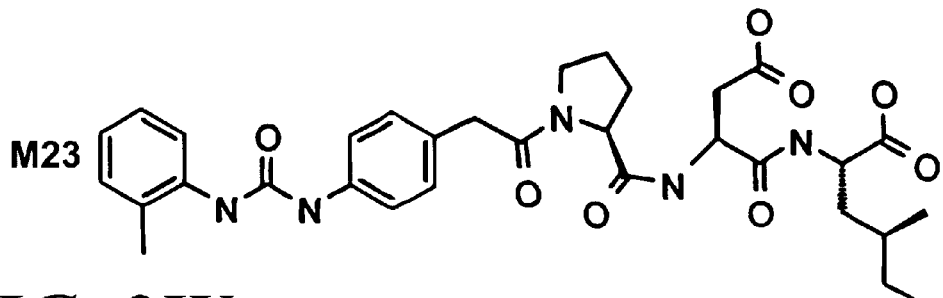
Figure 3X:
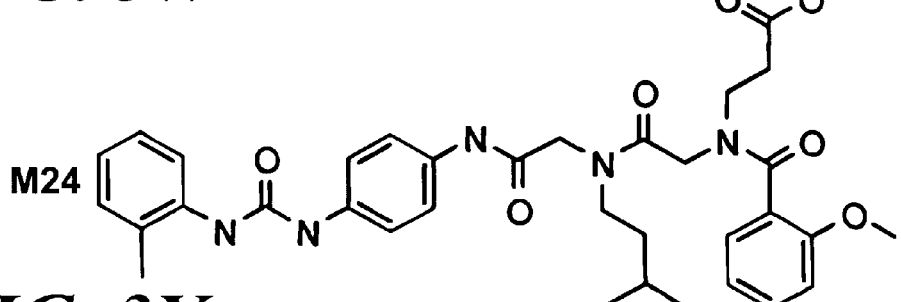
Figure 13:
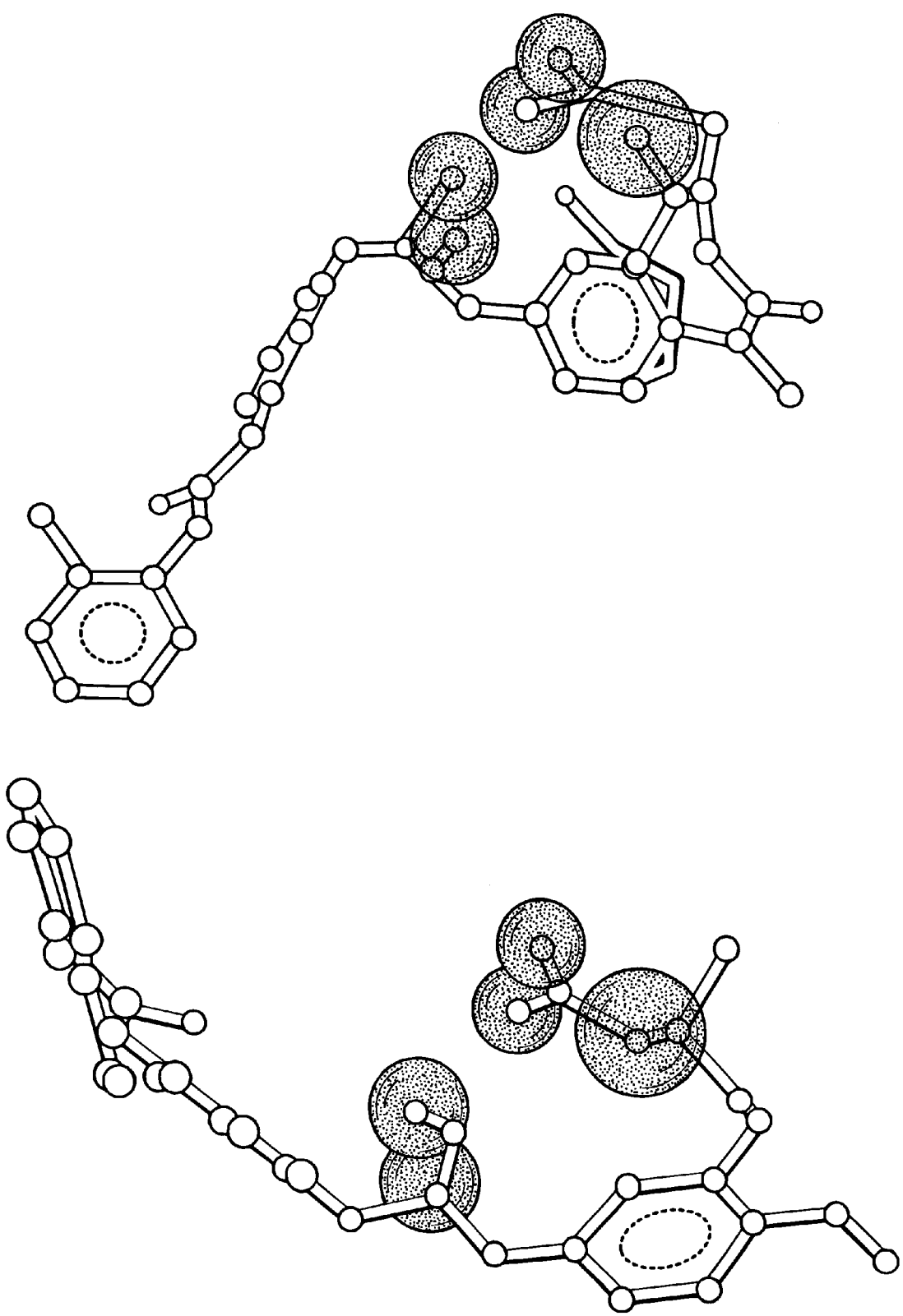
FIG. 13. Two potent VLA-4 inhibitors (M13 and M17) with the Model 3.
Figure 14:
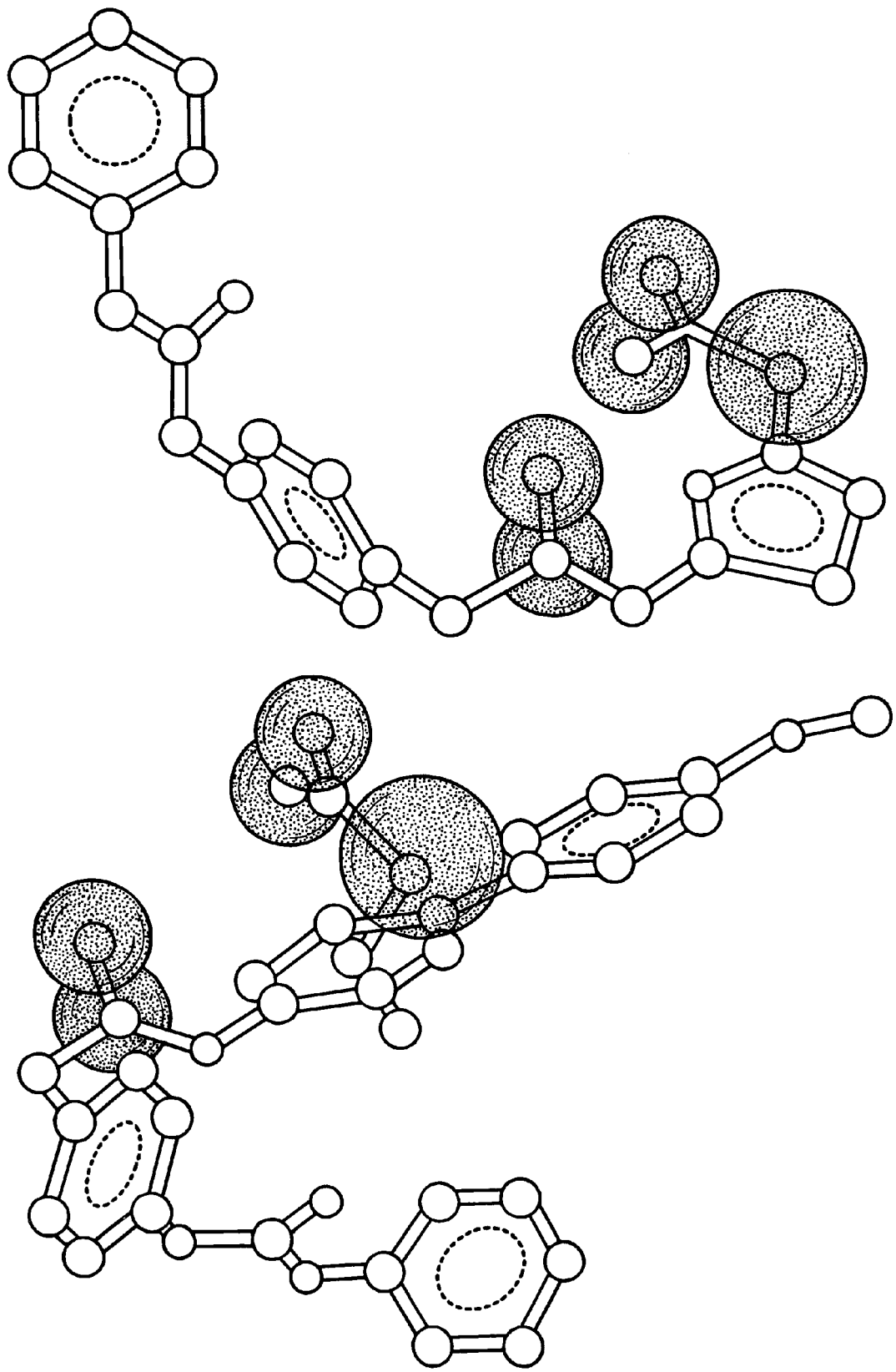
FIG. 14. The fit of two novel compounds to the Model 3. These were identified by searching through a commercially available database of scaffolds using Catalyst.
Figure 15A:
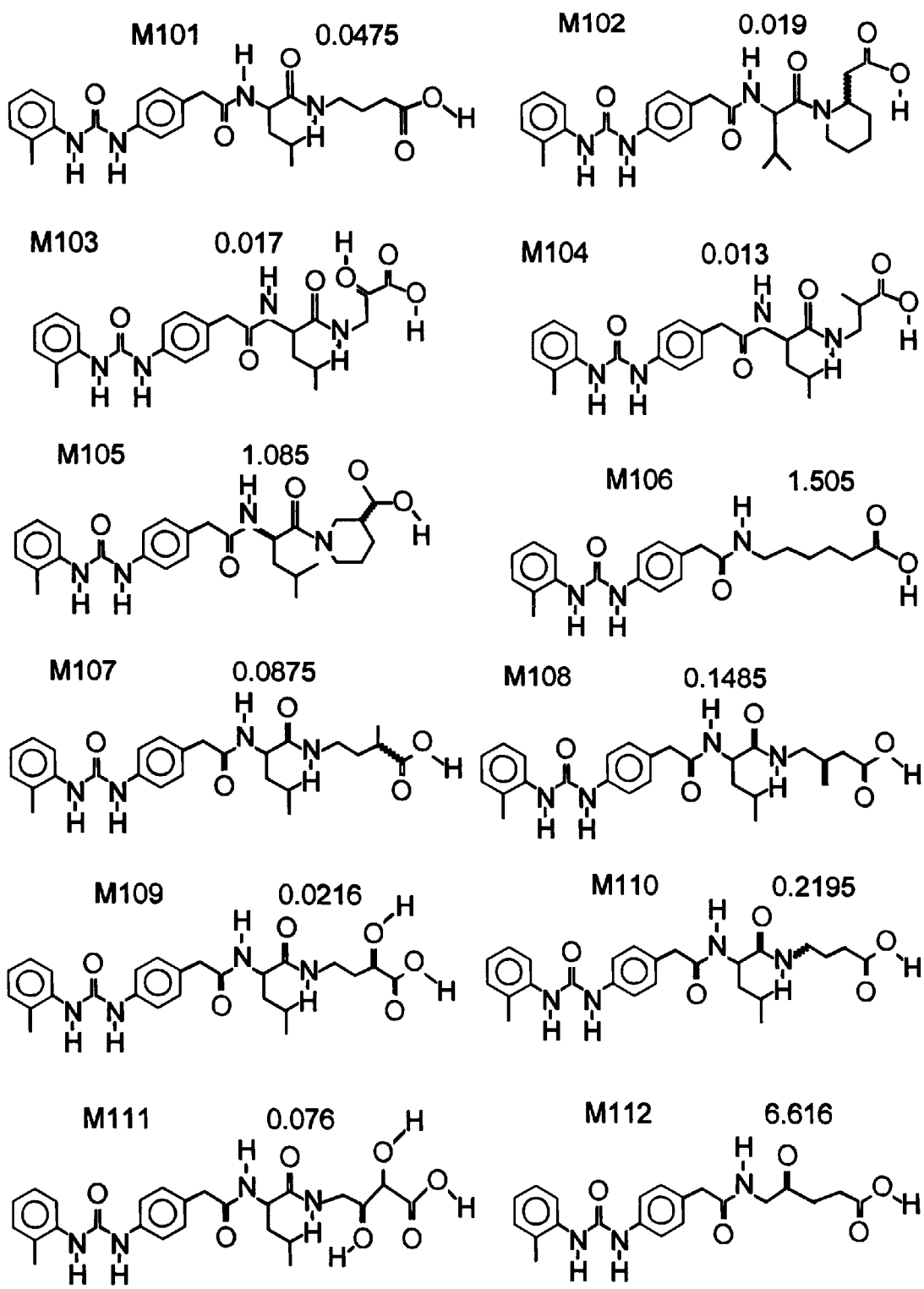
FIGS. 15(A)–(E). A list of preferred compounds of the claimed invention.
Figure 15B:
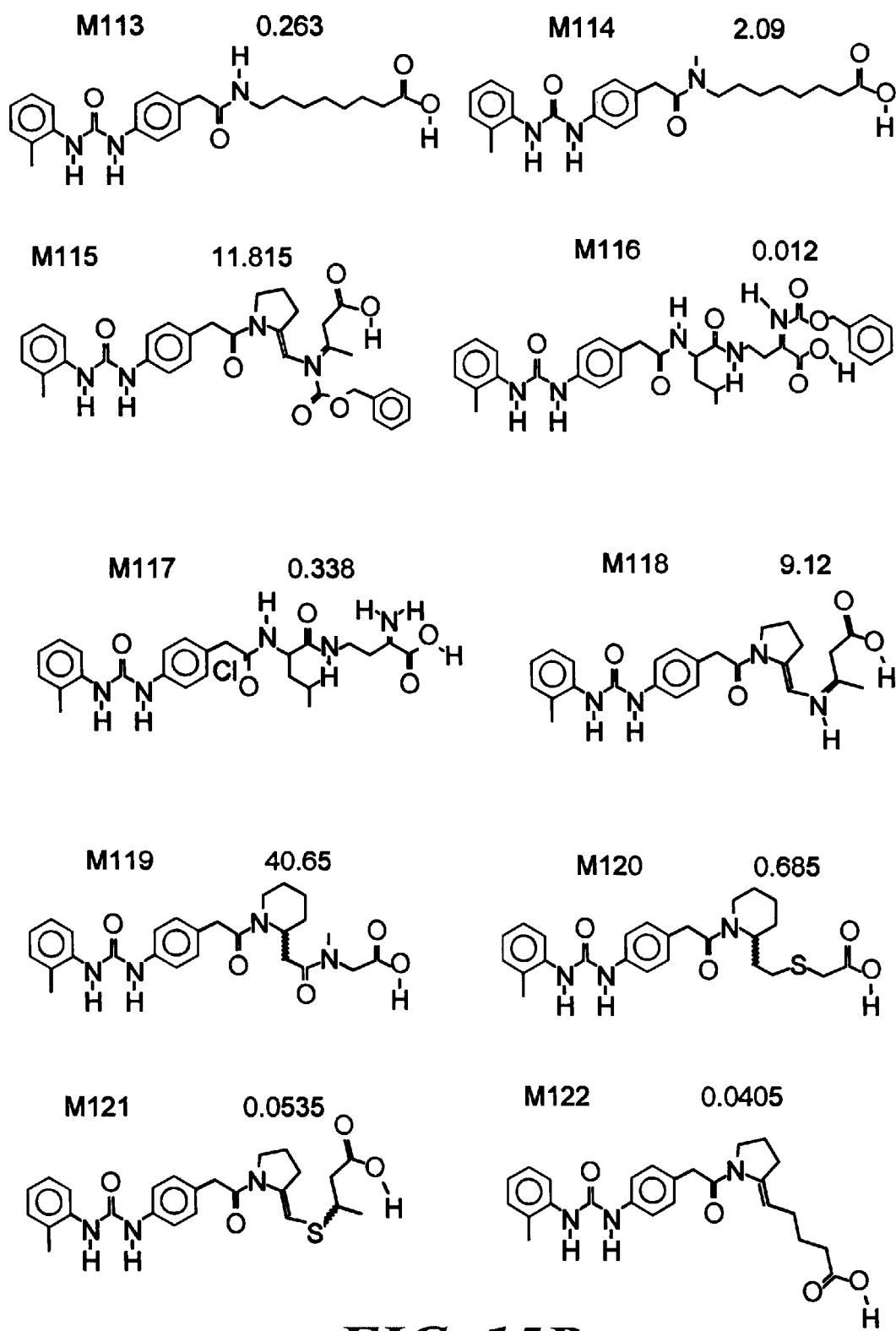
Figure 15C:
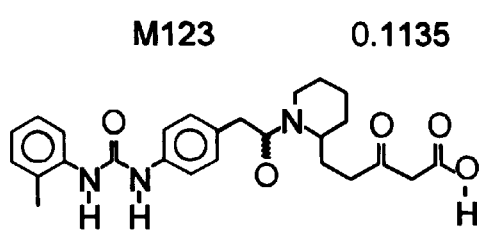
Figure 15C:
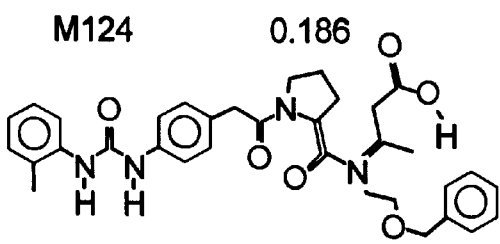
Figure 15C:
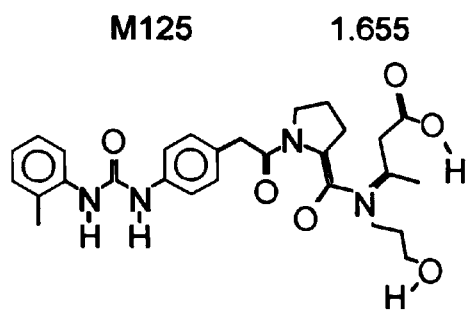
Figure 15C:
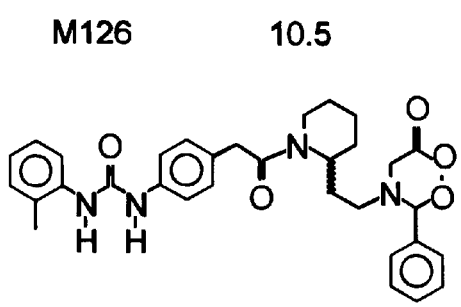
Figure 15C:
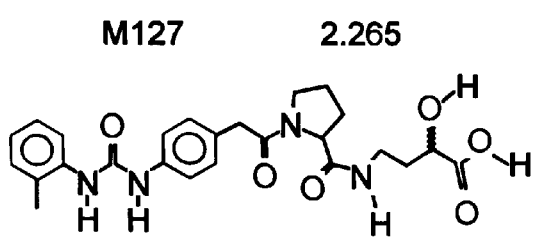
Figure 15C:
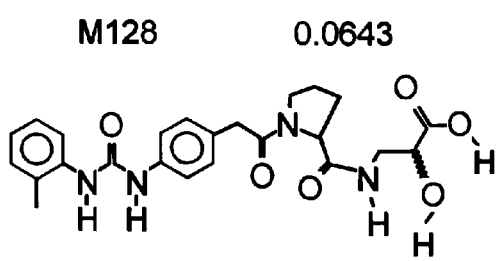
Figure 15C:
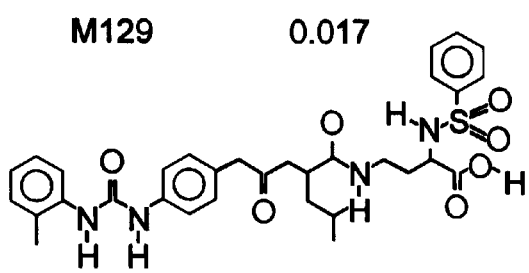
Figure 15C:
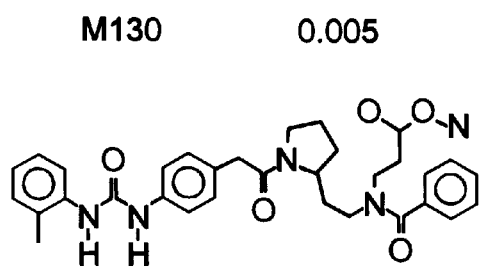
Figure 15C:
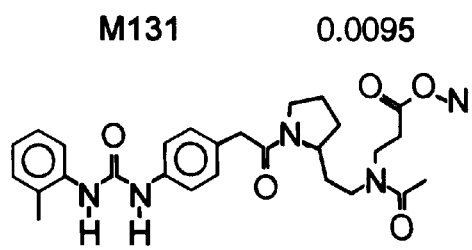
Figure 15C:
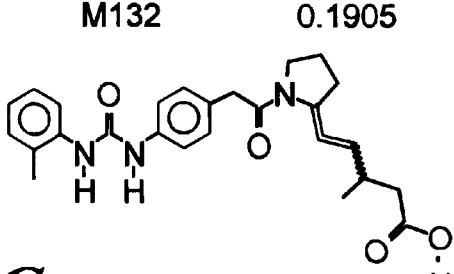
Figure 15D:
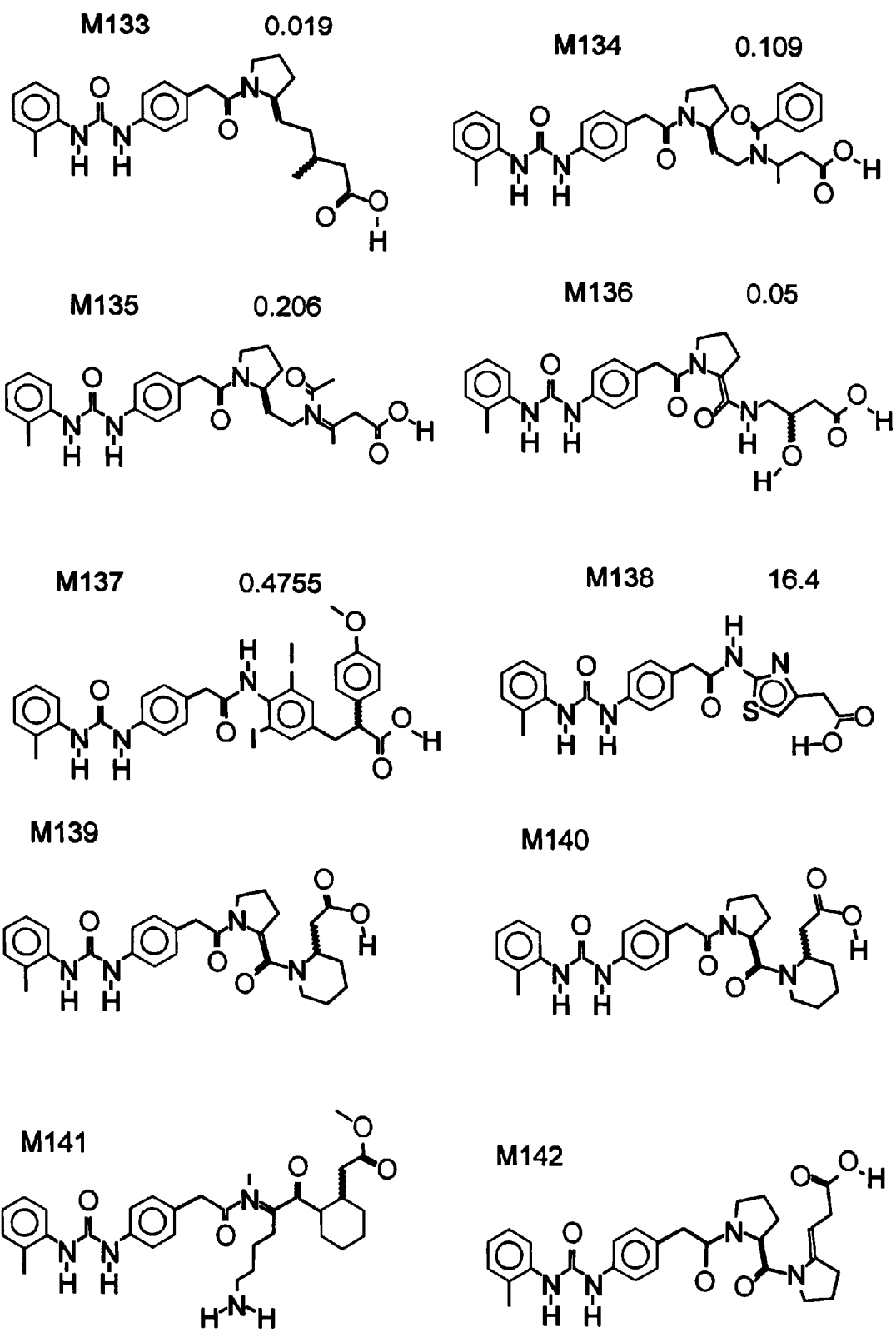
Figure 15E:
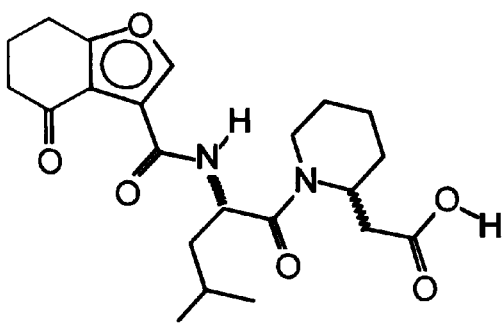
Figure 15E:
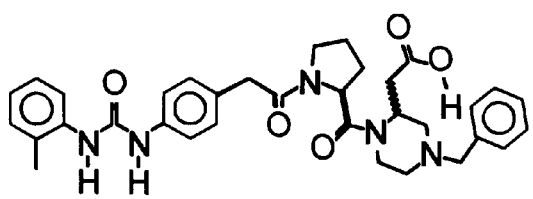
Figure 15E:
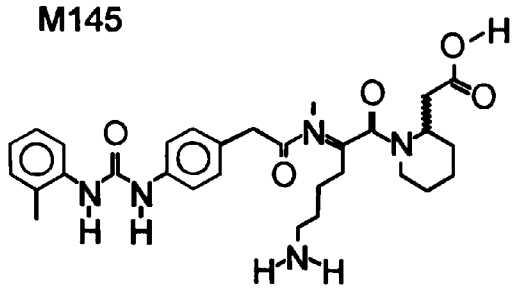
Figure 15E:
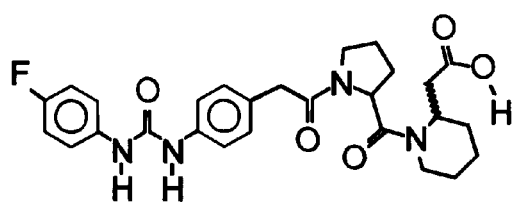
Figure 15E:
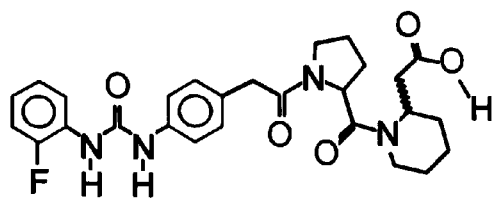
Figure 15E:
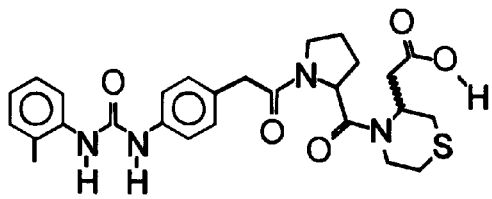
Figure 15E:
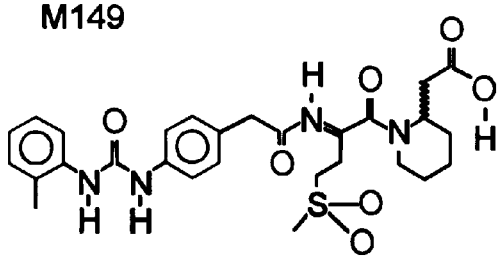
Figure 15E:
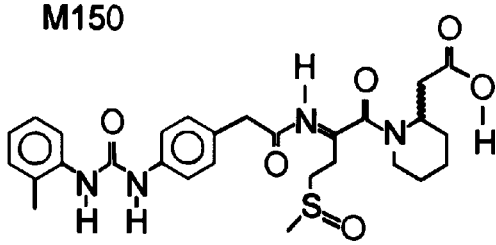

Applicants searched for scaffolds that could coordinate to a metal, using Model 3. In FIG. 13 they show how M13(FIG. 3m) and M14(FIG. 3n) fit the Model 3. Applicants also searched chemical databases for other molecules that fit Model 3. FIG. 14 shows two compounds that contain scaffolds that are commercially available and map to Model 3.

It will be apparent to those skilled in the art that various modifications and variations can be made in the claimed invention without departing from the spirit or scope of the invention. Thus, it is intended that the present invention encompass modifications and variations of the invention provided that they come within the scope of the appended claims and their equivalents.

What is claimed is:

1. A cell adhesion inhibitor of Formula GB-1

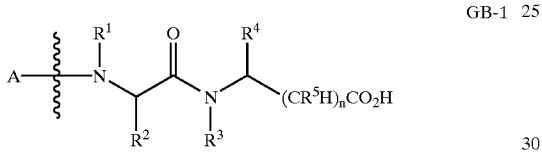

wherein A is selected from the group consisting of aliphatic acyl optionally substituted with N-alkyl- or N-arylamido, aroyl, heterocycloyl, alkyl- or arylsulfonyl, aralkylcarbonyl optionally substituted with aryl, heterocycloalkylcarbonyl, aralkyloxycarbonyl, cycloalkylcarbonyl optionally fused with aryl, heterocycloalkoxycarbonyl, alkylaminocarbonyl, arylamino carbonyl and aralkylaminocarbonyl optionally substituted with bis(alkylsulfonyl) amino, alkoxycarbonylamino or alkenyl, alkylsulfonyl, aralkylsulfonyl, arylsulfonyl, cycloalkylsulfonyl optionally fused with aryl, heterocyclylsulfonyl, heterocyclylalkylsulfonyl, aralkoxycarbonyl, aryloxycarbonyl, cycloalkyloxycarbonyl, heterocyclyloxycarbonyl, heterocyclylalkoxycarbonyl, mono- or di-alkylaminocarabonyl optionally substituted with aryl, (alkyl) (aralkyl) aminocarabonyl, mono- or di-aralkylaminocarbonyl, mono- or di-arylaminocarabonyl, (aryl) (alkyl) aminocarbonyl, mono- or di-cycloalkylaminocarbonyl, heterocyclylaminocarbonyl, heterocyclylalkylaminocarbonyl, (alkyl) (heterocyclyl) aminocarbonyl, (alkyl) (heterocyclylalkyl) aminocarbonyl, (aralkyl) (heterocyclyl) aminocarabonyl, (aralkyl) (heterocyclylalkyl) aminocarbonyl, alkenoyl optionally substituted with aryl, alkenylsulfonyl optionally substituted with aryl, alkynoyl optionally substituted with aryl, alkynylsulfonyl optionally substituted with aryl, cycloalkenylcarbonyl, cycloalkenylsulfonyl, cycloalkylalkanoyl, cycloalkylalkylsulfonyl, arylaroyl, biarylsulfonyl, alkoxysulfonyl, aralkoxysulfonyl, alkylaminosulfonyl, aryloxysulfonyl, arylaminosulfonyl, N-arylurea-substituted alkanoyl, N-arylurea-substituted alkylsulfonyl, cycloalkenyl-substituted carbonyl, cycloalkenyl-substituted sulfonyl, alkenoxycarbonyl optionally substituted with aryl, alkenoxysulfonyl optionally substituted with aryl, alkynoxycarbonyl optionally substituted with aryl, alkynoxysulfonyl optionally substituted with aryl, alkenyl- or alkynyl-aminocarbonyl optionally substituted with aryl, alkenyl- or alkynyl-aminosulfonyl optionally substituted with aryl, acylamino-substituted alkanoyl, acylamino-substituted alkylsulfonyl, aminocarbonyl-substituted alkanoyl, carbamoyl-substituted alkanoyl, carbamoyl-substituted alkylsulfonyl, heterocyclylalkanoyl, heterocyclylaminosulfonyl, carboxyalkyl-substituted aralkoyl, carboxyalkyl-substituted aralkylsulfonyl, oxocarbocyclyl-fused aroyl, oxocarbocyclyl-fused arylsulfonyl, heterocyclylalkanoyl, N',N'-alkyl, arylhydrazinocarbonyl, aryloxy-substituted alkanoyl and heterocyclylalkylsulfonyl, alkenyl, alkynyl, cycloalkyl, aryl-fused cycloalkyl, cycloalkenyl, aryl, aryl-substituted alkyl ("aralkyl"), aryl-substituted alkenyl or alkynyl, cycloalkyl-substituted alkyl, cycloalkenyl-substituted cycloalkyl, biaryl, alkoxy, alkenoxy, alkynoxy, aryl-substituted alkoxy ("aralkoxy"), aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarabonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl;

n is 1–4;

$R^1$ and $R^4$ are each independently selected from the group consisting of H, aryl, aralkyl, and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, carboxamide, amine, alkylsulfone, or alkylsulfoxide;

$R^2$ is selected from the group consisting of H and alkyl optionally substituted with amine, cycloalkyl, alkylsulfone, or alkylsulfoxide;

$R^3$ is selected from the group consisting of H and alkyl optionally substituted with aralkoxy or hydroxy;

$R^1$ and $R^2$ may be taken together to form —$(CR^1R^2)_p$— or —$(CR^1R^2)_qX(CR^1R^2)_r$—;

R³ and R⁴ may be taken together to form —(CR¹R²)$_m$—
or —(CR¹R²)$_q$X(CR¹R²)$_r$—;

R³ and R⁵ may be taken together to form —(CR¹R²)$_m$—;

X is selected from the group consisting of —CH$_2$—, S, O, NR⁴, NCOR⁷, and NSO$_2$R⁷;

m is 3 or 4;

p is 3 or 4;

q and r are independently 1 or 2;

R⁵ is selected from the group consisting of H, hydroxy, alkyl, NH$_2$, NHSO$_2$R⁷, NHCOR⁷, and HCO$_2$R⁷;

R⁷ is selected from the group consisting of aryl aralkyl, and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, and carboxamide;

provided that when R³ is H, n is 2–4; or when n is 1, only R³ or R⁵ is H.

2. The compound of claim 1, wherein A is selected from the group consisting of alkyl- or arylsulfonyl; alkylsulfonyl; aralkylsulfonyl; arylsulfonyl; cycloalkylsulfonyl optionally fused with aryl; heterocyclylsulfonyl; heterocyclylalkylsulfonyl; alkenylsulfonyl optionally substituted with aryl; alkynylsulfonyl optionally substituted with aryl; cycloalkenylsulfonyl; cycloalkylalkylsulfonyl; biarylsulfonyl; alkoxysulfonyl; aralkoxysulfonyl; alkylaminosulfonyl; aryloxysulfonyl; arylaminosulfonyl; N-arylurea-substituted alkylsulfonyl; cycloalkenyl-substituted sulfonyl; alkenoxysulfonyl optionally substituted with aryl; alkynoxysulfonyl optionally substituted with aryl; alkenyl- or alkynyl-aminosulfonyl optionally substituted with aryl; acylamino-substituted alkylsulfonyl; carbamoyl-substituted alkylsulfonyl; heterocyclylaminosulfonyl; carboxyalkyl-substituted aralkylsulfonyl; oxocarbocyclyl-fused arylsulfonyl; and aryloxy-substituted heterocyclylalkylsulfonyl.

3. The compound of claim 1, wherein A is aliphatic acyl, aroyl, aralkylcarbonyl, heterocycloyl, alkoxycarbonyl, aralkyloxycarbonyl, or heterocycloalkylcarbonyl.

4. The compound of claim 1, wherein A is aralkylcarbonyl.

5. The compound of claim 1, wherein A contains a diphenylurea moiety.

6. The compound of claim 1, wherein A is o-methylphenyl-ureido-phenylmethyl.

7. The compound of claim 1, wherein R¹ is H or alkyl.

8. The compound of claim 1, wherein R² is H, alkyl, alkyl substituted with amino or alkylsulfone.

9. The compound of claim 1, wherein R¹ and R² are taken together to form—(CR¹R²)$_p$—, or —(CR¹R²)$_q$X(CR¹R²)$_r$—.

10. The compound of claim 9, wherein R¹ and R² are taken together to form —(CH$_2$)$_p$—, or —(CH$_2$)$_q$X(CH$_2$)$_r$—, where X is S, O, or NR⁴.

11. The compound of claim 1, wherein R³ is H or alkyl.

12. The compound of claim 1, wherein R⁴ is H or alkyl.

13. The compound of claim 1, wherein R³ and R⁴ are taken together to form—(CR¹R²)$_p$—, or —(CR¹R²)$_q$X(CR¹R²)$_r$—.

14. The compound of claim 13, wherein R³ and R⁴ are taken together to form —(CH$_2$)$_p$—, or —(CH2)$_q$X(CH$_2$)$_r$—, where X is S, O, or NR⁴.

15. The compound of claim 1, wherein R⁵ is H, hydroxy, alkyl, NHCOR⁷, or NHSO$_2$R⁷.

16. The compound of claim 15, wherein R⁷ is alkyl, aryl, or aralkyl.

17. The compound of claim 1, wherein R⁴ is H and R⁵ is NHCOR⁷, where R⁷ is alkyl, aryl, or aralkyl.

18. The compound of claim 1, wherein R⁴ is H and R⁵ is NHSO$_2$R⁷, where R⁷ is alkyl, aryl, or aralkyl.

19. The compound of claim 1, wherein A is aralkylcarbonyl; R¹ is H or alkyl; R² is H, alkyl, alkyl substituted with amino or alkylsulfone; R³ is H or alkyl; R⁴ is H or alkyl; R⁵ is H, hydroxy, alkyl, NHCOR⁷, or NHSO$_2$R⁷, in which R⁷ is alkyl, aryl, or aralkyl; R¹ and R² optionally taken together to form —(CH$_2$)$_p$—, or —(CH$_2$)$_q$X(CH$_2$)$_r$—, where X is S, O, or NR⁴; and R³ and R⁴ optionally taken together to form —(CH$_2$)$_p$—, or —(CH$_2$)$_q$X(CH$_2$)$_r$—, where X is S, O, or NR⁴.

20. The compound of claim 1, said compound is selected from the group consisting of the formulas M101–M105, M107–M111, M117, M124, M125, M127, M128, M139–M141, M142–M150.

* * * * *